United States Patent
Widdison

(10) Patent No.: US 9,901,647 B2
(45) Date of Patent: Feb. 27, 2018

(54) CONJUGATES COMPRISING CELL-BINDING AGENTS AND CYTOTOXIC AGENTS

(71) Applicant: ImmunoGen, Inc., Waltham, MA (US)

(72) Inventor: Wayne C. Widdison, Belmont, MA (US)

(73) Assignee: IMMUNOGEN, INC., Waltham, MA (US)

(*) Notice: Subject to any disclaimer, the term of this patent is extended or adjusted under 35 U.S.C. 154(b) by 0 days.

(21) Appl. No.: 14/763,612

(22) PCT Filed: Feb. 28, 2014

(86) PCT No.: PCT/US2014/019508
§ 371 (c)(1),
(2) Date: Jul. 27, 2015

(87) PCT Pub. No.: WO2014/134486
PCT Pub. Date: Sep. 4, 2014

(65) Prior Publication Data
US 2015/0359904 A1    Dec. 17, 2015

Related U.S. Application Data

(60) Provisional application No. 61/819,848, filed on May 6, 2013, provisional application No. 61/770,937, filed on Feb. 28, 2013.

(51) Int. Cl.
*A61K 31/535* (2006.01)
*A61K 47/48* (2006.01)
*A61K 31/5365* (2006.01)
*C07D 403/06* (2006.01)
*C07D 403/12* (2006.01)

(52) U.S. Cl.
CPC .... *A61K 47/48384* (2013.01); *A61K 31/5365* (2013.01); *A61K 47/48569* (2013.01); *C07D 403/06* (2013.01); *C07D 403/12* (2013.01)

(58) Field of Classification Search
None
See application file for complete search history.

(56) References Cited

FOREIGN PATENT DOCUMENTS

| EA | 0453082 A1 | 10/1991 |
|---|---|---|
| EP | 0446071 A2 | 9/1991 |
| WO | WO-2000/044788 A1 | 8/2000 |
| WO | WO-2003/011909 A1 | 2/2003 |
| WO | WO-2005/117986 A2 | 12/2005 |
| WO | WO-2006/034488 A2 | 3/2006 |
| WO | WO-2007/140371 A2 | 12/2007 |
| WO | WO-2009/077438 A1 | 6/2009 |
| WO | WO-2009/099728 A1 | 8/2009 |
| WO | WO-2011/156328 A1 | 12/2011 |
| WO | WO-2012/061590 A1 | 5/2012 |
| WO | WO-2012/145112 A2 | 10/2012 |

OTHER PUBLICATIONS

CAS RN 198986-54-8 (entered into STN Dec. 24, 1997).*
CAS RN 133338-37-1 (entered into STN Apr. 19, 1991).*
King et al.; "Improved tumor targeting with chemically cross-linked recombinant antibody fragments"; Cancer Research, 54(23):6176-6185 (1994).

* cited by examiner

*Primary Examiner* — Craig Ricci
(74) *Attorney, Agent, or Firm* — McCarter & English, LLP; Yu Lu; Xin Zhang

(57) ABSTRACT

The invention provides linker compounds and cytotoxic compounds that are useful for forming a CBA-drug conjugates; and conjugates so formed. Such conjugates and/or cytotoxic compounds may be effective for treating a range of diseases, such as cancer, with a relatively high activity at a relatively low, non-toxic dose.

4 Claims, 6 Drawing Sheets v = 0 or an integer from 1 to 10 (preferably, v is 0, 2, 3, 4, 5, 6, 7, 8, 9 or 10)

SEQUENCE LISTING

<160> NUMBER OF SEQ ID NOS: 4

<210> SEQ ID NO 1
<211> LENGTH: 4
<212> TYPE: PRT

-continued

```
<213> ORGANISM: Artificial Sequence
<220> FEATURE:
<223> OTHER INFORMATION: Oligopeptide

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(1)
<223> OTHER INFORMATION: Xaa is beta-Ala

<400> SEQUENCE: 2

Xaa Leu Ala Leu
1

<210> SEQ ID NO 3
<211> LENGTH: 4
<212> TYPE: PRT
<213> ORGANISM: Artificial Sequence
<220> FEATURE:
<223> OTHER INFORMATION: Oligopeptide

<400> SEQUENCE: 3

Gly Phe Leu Gly
1

<210> SEQ ID NO 4
<211> LENGTH: 4
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(1)
<223> OTHER INFORMATION: Xaa is beta-Ala

<400> SEQUENCE: 4

Xaa Gly Gly Gly
1
```

CONJUGATES COMPRISING CELL-BINDING AGENTS AND CYTOTOXIC AGENTS

REFERENCE TO RELATED APPLICATIONS

This application is a U.S. national stage filing under 35 U.S.C. § 371, of International Application No. PCT/US2014/019508, filed on Feb. 28, 2014, which claims the benefit of the filing date, under 35 U.S.C. § 119(e), of U.S. Provisional Application No. 61/770,937, filed on Feb. 28, 2013, and U.S. Provisional Application No. 61/819,848, filed on May 6, 2013, the entire contents of each of which are incorporated herein by reference.

BACKGROUND OF THE INVENTION

Antibody-drug conjugates (ADC) and cell binding agent-drug conjugates are emerging as a powerful class of anti-tumor agents with efficacy across a range of cancers. The cell binding agent-drug conjugates (such as ADCs) are commonly composed of three distinct elements: a cell-binding agent (e.g., antibody); a linker; and a cytotoxic moiety. The linker component of ADC is an important element in developing targeted anti-cancer agents that possess an optimal therapeutic window, i.e., therapeutic activity at a low, non-toxic dose.

Therefore, there is a need for targeted therapies such as ADCs and other cell binding agent-drug conjugates having a new class of linker components.

SUMMARY OF THE INVENTION

A first embodiment of the invention features a conjugate represented by the following formula, or a pharmaceutically acceptable salt thereof:

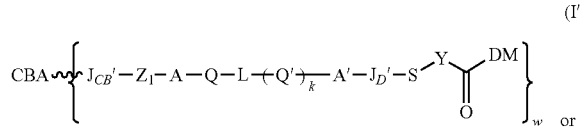

(I')

or

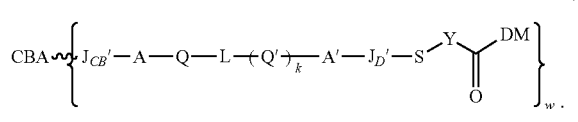

(I)

In Formula (I') or (I) above, CBA is a cell binding agent; DM is a drug moiety represented by the following formula:

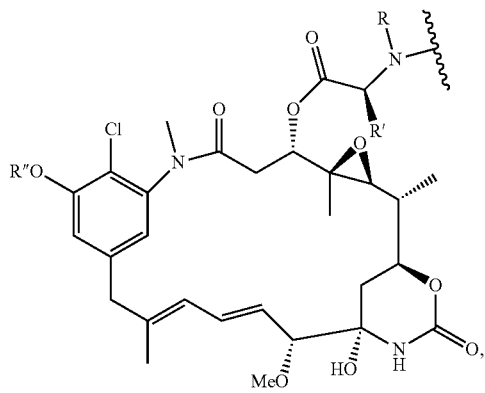

(II)

in which R, R', and R", for each occurrence, are independently H or an optionally substituted alkyl; Y is $-(CR_3R_4)_iCR_1R_2-$; $R_1$ to $R_4$, for each occurrence, are independently H, an optionally substituted alkyl, an optionally substituted alkenyl, an optionally substituted cycloalkyl, an optionally substituted heterocyclyl, an optionally substituted aryl, or an optionally substituted heteroaryl; i is an integer between 0 and 15; $J_{CB'}$ is

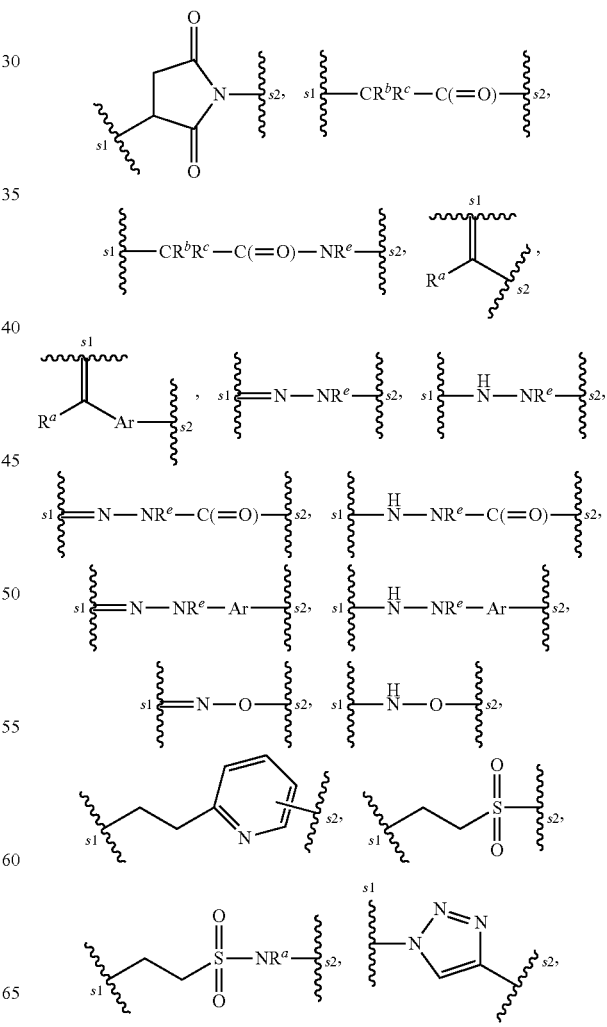

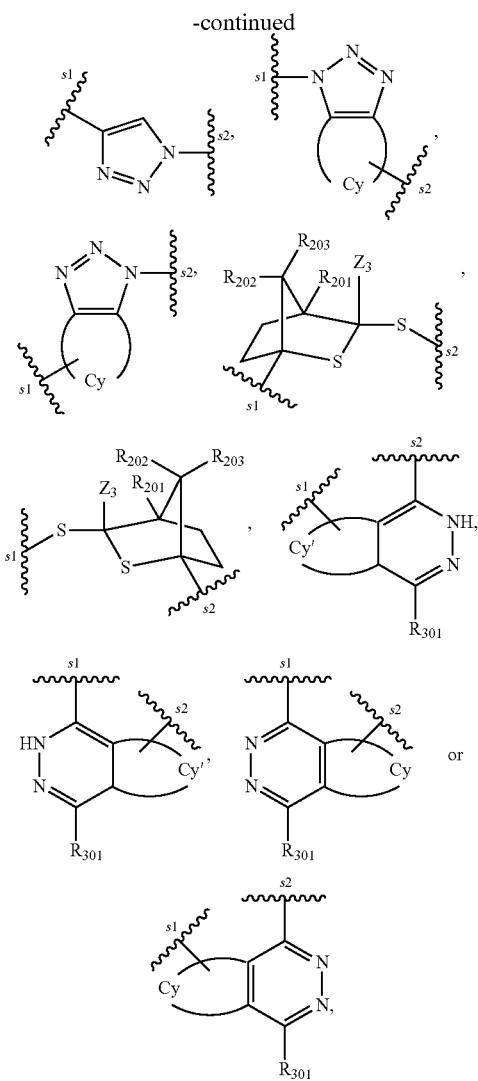

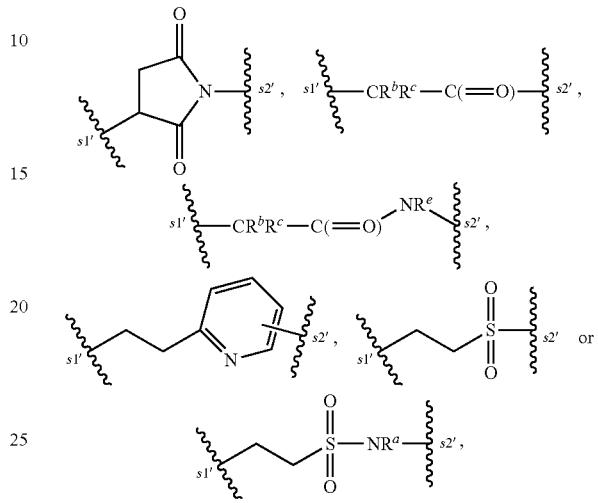

are independently H or an optionally substituted alkyl; $Z_1$ in Formula (I') is absent, $-SO_2NR_9-$, $-NR_9SO_2-$, $-C(=O)-NR_9$, $-NR_9-C(=O)-$, $-C(=O)-O-$, $-O-C(=O)-$, $-CH_2-O-$, $-O-CH_2-$, $-(CH_2CH_2O)_p-$ or $-(OCH_2CH_2)_{p'}-$, wherein p and p' are independently an integer from 1 to 1000; $J_{D'}$ is in which s1' is the site covalently linked to sulfur atom, s2' is the site covalently linked to the group A'; A and A' are each independently an optionally substituted alkylene, an optionally substituted alkenylene, an optionally substituted alkynylene, an optionally substituted cycloalkylene, an optionally substituted cycloalkenylene or an optionally substituted cycloalkynylene; Q is $-Z_1-P-Z_2-$; Q' is $-Z_1'-P'-Z_2'-$; one of $Z_1$ and $Z_2$ is $-C(=O)-$, and the other is $-NR^h-$; one of $Z_1'$ and $Z_2'$ is $-C(=O)-$, and the other is $-NR^{h'}$; P and P' are each independently absent, an optionally substituted alkylene, $-(CH_2-CH_2-O)_j-$, $-(O-CH_2-CH_2)_j-$, or $[XX]_{1-10}$, in which each XX is a residue of an independently selected amino acid; j is an integer between 1 and 500; k is 0 or 1; L is $-(CR_5R_6)_v-$, $-(CR_7R_8)_q-N(R^g)-(CR_9R_{10})_r-$, $-(CR_7R_8)_q-C(R^a)(R^g)-(CR_9R_{10})_r$ or $-(CR_{11}R_{12})_s-N(R^g)-(CR_{13}R_{14})_t-N(R^{g'})-(CR_{15}R_{16})_u-$; $R^g$ and $R^{g'}$ are each independently $-(CR_{17}R_{18})_p-Z-V$; p is an integer between 1 and 5; V is H, a charged substituent or an ionizable group; Z is absent, $-C(=O)NR^h$-alkylene- or $-NR^h-C(=O)$-alkylene-; $R^h$ and $R^{h'}$, for each occurrence, are independently H or an optionally substituted alkyl; $R_5$ to $R_{18}$, for each occurrence, are independently H or an optionally substituted alkyl; q, r, s, t, u and v are each independently an integer between 0 and 10 (preferably an integer between 0 to 5); and w is an integer between 1 and 20.

in which s1 is the site covalently linked to the CBA, s2 is the site covalently linked to the group $Z_1$ in formula (I') or the group A in formula (I), Ar is an optionally substituted arylene or an optionally substituted heteroarylene, Cy is the non-alkyne residue of an optionally substituted cycloalkyne or an optionally substituted heterocycloalkyne (see below in the third embodiment); $R_{201}$, $R_{202}$ and $R_{203}$ each are independently H or an optionally substituted alkyl (preferably, $R_{201}$, $R_{202}$ and $R_{203}$ are all H; or $R_{201}$ is $-CH_3$ and $R_{202}$ and $R_{203}$ are both H); $Z_3$ is pyridyl or

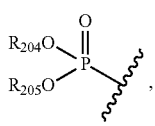

wherein $R_{204}$ and $R_{205}$ are each independently optionally substituted alkyl (preferably, $R_{204}$ and $R_{205}$ are both methyl or ethyl) and Cy' is the non-alkene residue of an optionally substituted strained cycloalkene or an optionally substituted strained heterocycloalkene (see below in the second embodiment); and $R_{301}$ is H or optionally substituted alkyl (preferably $R_{301}$ is H); $R^a$, $R^b$, $R^c$, and $R^e$, for each occurrence, A second embodiment of the invention features another conjugate represented by the following formula, or a pharmaceutically acceptable salt thereof:

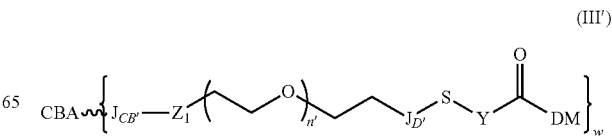

(III')

-continued

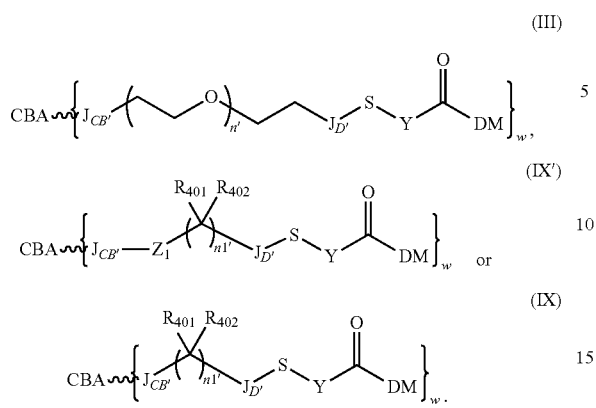

(III)

(IX')

(IX)

In Formula (III'), (III), (IX) or (IX') above, n' is an integer between 1 and 500; n1' is an integer from 1 to 20; $R_{401}$ and $R_{402}$ are each independently H or an optionally substituted alkyl (preferably, $R_{401}$ and $R_{402}$ are both H); $J_{CB'}$ is

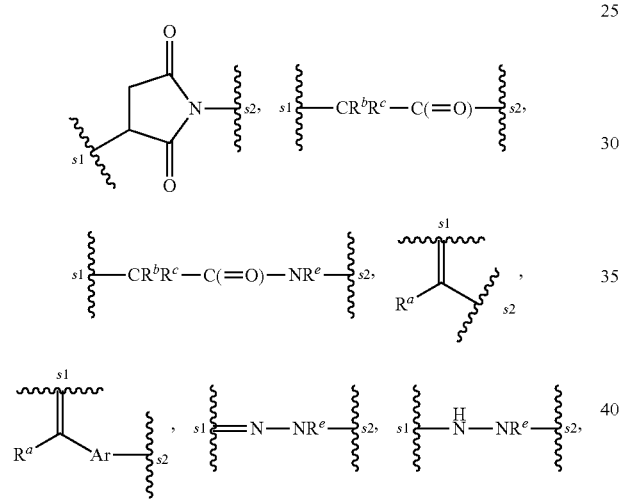

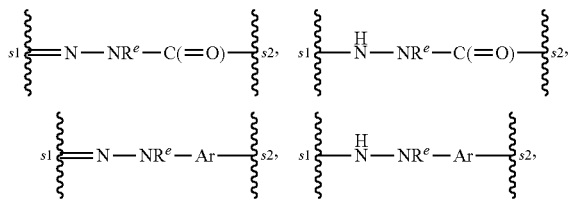

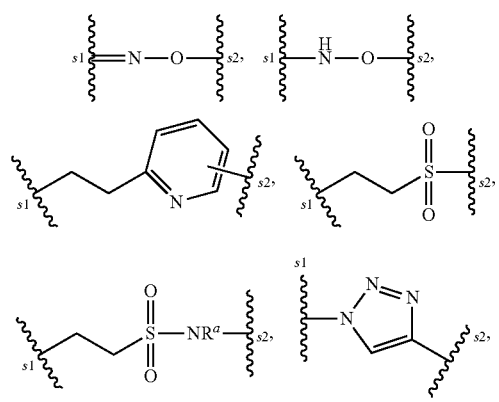

-continued

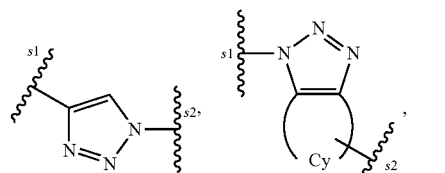

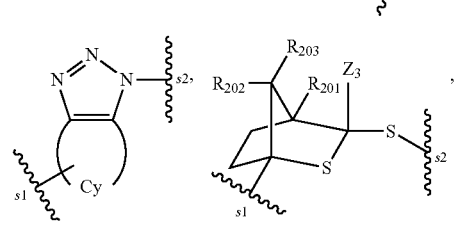

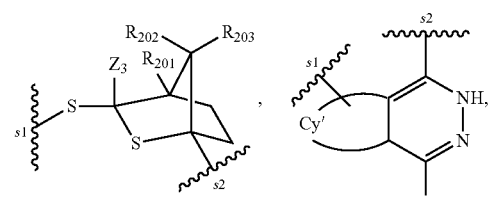

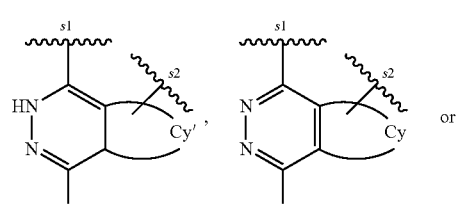

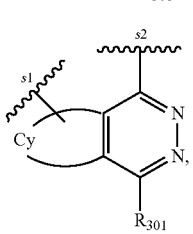

in which s1 is the site covalently linked to the CBA, s2 is the site covalently linked to the $Z_1$ group in Formulae (III') and (IX'), the $-(CH_2-CH_2-O)_n$ group in Formula (III), or the $(CR_{401}R_{402})_{n1'}$ group in Formula (IX); and $J_{D'}$ is

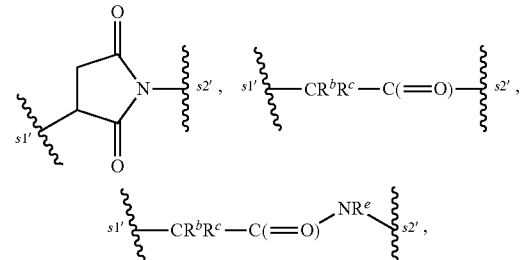

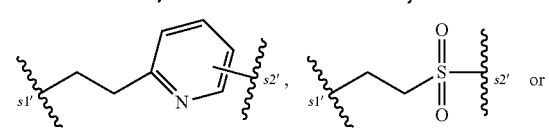

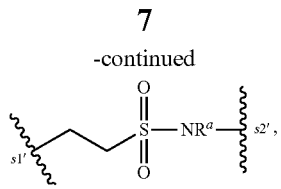

in which s1' is the site covalently linked to sulfur atom, s2' is the site covalently linked to the ethylene group in Formulae (III) and (III') or the $(CR_{401}R_{402})_{n1}$ group in Formulae ((IX) and (IX')). In this second embodiment, the remainder of the variables are as defined in the first embodiment above.

A third embodiment of the invention features a cytotoxic compound represented by the following formula, or a salt (e.g., a pharmaceutically acceptable salt) thereof:

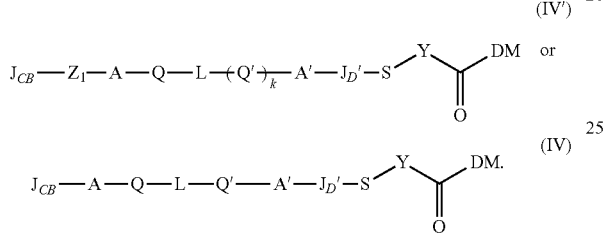

In Formula (IV') or (IV) above, $J_{CB}$ is maleimide,

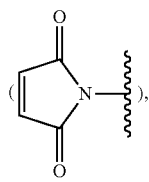

$X'—CR^bR^c—C(=O)—$, $X'—CR^bR^c—C(=O)—NR^e—$, $R^a—C(=O)—$, $R^a—C(=O)—Ar—$, $NH_2—NR^e—$, $NH_2—NR^e—C(=O)—$, $NH_2—NR^e—Ar—$, $NH_2—O—$,

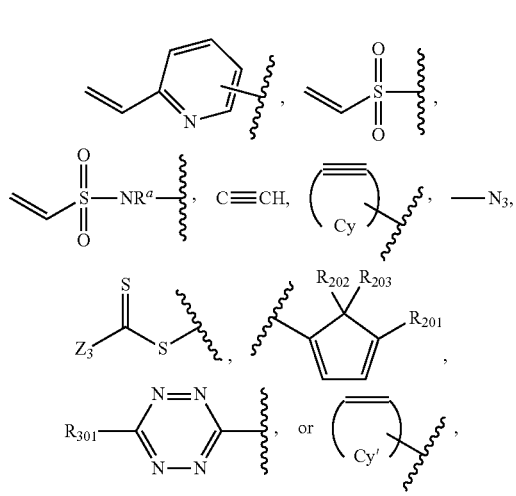

in which X' is a halogen;

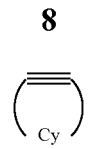

is an optionally substituted cycloalkyne or an optionally substituted heterocycloalkyne,

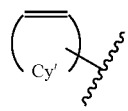

is an optionally substituted strained cycloalkene or an optionally substituted strained heterocycloalkene, and the remainder of the variables are as defined in the first embodiment.

Preferably, for Formula (IV') or (IV) above,

is an optionally substituted cycloalkyne or an optionally substituted heterocycloalkyne that can readily react with an azide to form a triazole through copper free click chemistry or can readily react with a tetrazine (see, for example, *J. Am. Chem. Soc.* 2012, 134, 9199-9208; WO 2011/136645; US 2009/0068738, Lang K. et al., *J. Am. Chem. Soc.* 2012, 134, 10317-10320, the entire teaching of these references are incorporated herein by its entirety). More preferably,

is cyclooctyne. In another preferred embodiment,

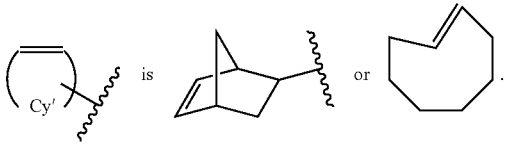

A fourth embodiment of the invention features another cytotoxic compound represented by the following formula, or a salt (e.g., a pharmaceutically acceptable salt) thereof:

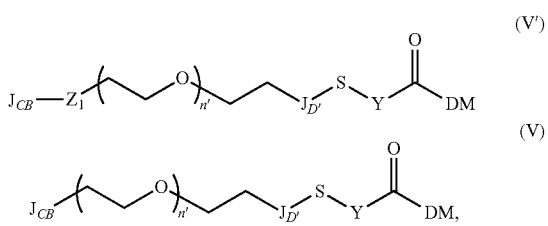

-continued

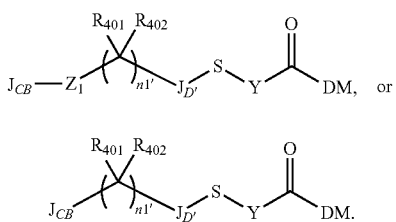 (X')

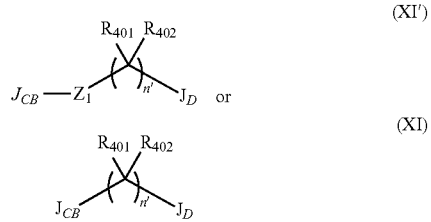 (XI')

(XI)

(X)

In Formula (V'), (V), (X') or (X) above, $J_{CB}$ is as defined in the third embodiment and the remainder of the variables are as defined in the second embodiment.

A fifth embodiment of the invention features a linker compound represented by the following formula, or a salt (e.g., a pharmaceutically acceptable salt) thereof:

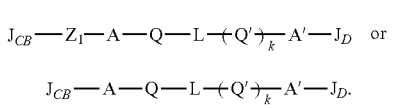

(VI')

(VI)

In Formula (VI') or (VI), $J_D$ is maleimide

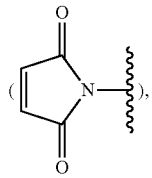

$X'$—$CR^bR^c$—$C(=O)$—, $X'$—$CR^bR^c$—$C(=O)$—$NR^e$—,

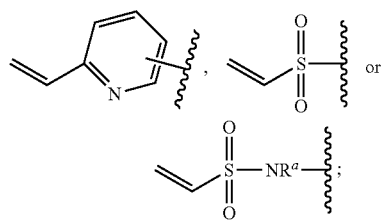 or $J_{CB}$ and X' are as defined in the third embodiment above; and the remainder of the variables are as defined in the first embodiment above.

A sixth embodiment of the invention features another linker compound represented by the following formula, or a salt (e.g., a pharmaceutically acceptable salt) thereof:

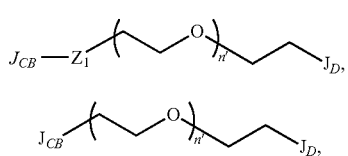

(VII')

(VII)

provided that $J_{CB}$ and $J_D$ are not both maleimide.

In Formula (VII'), (VII), (XI') or (XI), $J_D$ is as defined in the fifth embodiment above, $J_{CB}$ is as defined in the third embodiment above, and n' is as defined in the second embodiment.

In an alternative embodiment, in Formula (I'), (I), (III'), (III), (IV'), (IV), (V'), (V), (VI'), (VI), (VII') or (VII), Ar is phenylene. In another alternative embodiment, in Formula (III'), (III), (V'), (V), (VII') or (VII), n' is an integer between 1 and 400, between 1 and 300, between 1 and 200, between 1 and 100, between 1 and 50, between 1 and 30, between 1 and 15, between 2 and 10, or between 2 and 8 (e.g., 2, 3, 4, 5, 6, 7 or 8. In yet another alternative embodiment, in Formula (IX'), (IX), (X'), (X), (XI') or (XI), n1' is an integer between 1 and 10, between 2 and 8 (e.g., 2, 3, 4, 5, 6, 7 or 8). In yet another alternative embodiment, in Formula (III'), (III), (V'), (V), (VII') or (VII), Ar is phenylene, and n' is an integer between 1 and 400, between 1 and 300, between 1 and 200, between 1 and 100, between 1 and 50, between 1 and 30, between 1 and 15, between 2 and 10, or between 2 and 8 (e.g. 2, 3, 4, 5, 6, 7 or 8). In yet another embodiment, in Formula (IX'), (IX), (X'), (X), (XI') or (XI), Ar is phenylene, and n1' is an integer between 1 and 10, between 2 and 8 (e.g., 2, 3, 4, 5, 6, 7 or 8). In each of the alternative embodiments above, the remainder of the variables are as defined in the first, second, third, or fifth embodiment.

In an alternative embodiment, in Formula (I'), (I), (IV'), (IV), (VI') or (VI), L is absent.

Also within the scope of this invention is a composition (e.g., a pharmaceutical composition) comprising a conjugate represented by Formula (I'), (I), (III'), (III), (IX') or (IX), a cytotoxic compound represented by Formula (IV'), (IV), (V'), (V), (X') or (X) or a salt (e.g., a pharmaceutical acceptable salt) thereof. The composition may also include a carrier (e.g., a pharmaceutically acceptable carrier). The composition can further include a second therapeutic agent.

The present invention also includes a method of inhibiting abnormal cell growth or treating a proliferative disorder, a destructive bone disorder, an autoimmune disorder, a graft versus host disease, a transplant rejection, an immune deficiency, an inflammatory diseases, an infectious disease, a viral disease, a fibrotic disease, a neurodegenerative disorder, pancreatitis, or a kidney disease in a mammal (e.g., human), comprising administering to said mammal a therapeutically effective amount of a conjugate represented by Formula (I'), (I), (III'), (III), (IX') or (IX), a cytotoxic compound represented by Formula (IV'), (IV), (V'), (V), (X') or (X) or a salt (e.g., a pharmaceutical acceptable salt) thereof.

In a related embodiment, the method described above further comprises administering to said mammal sequentially or consecutively a second therapeutic (e.g., chemotherapeutic) agent.

DETAILED DESCRIPTION OF THE INVENTION

Figure 1:
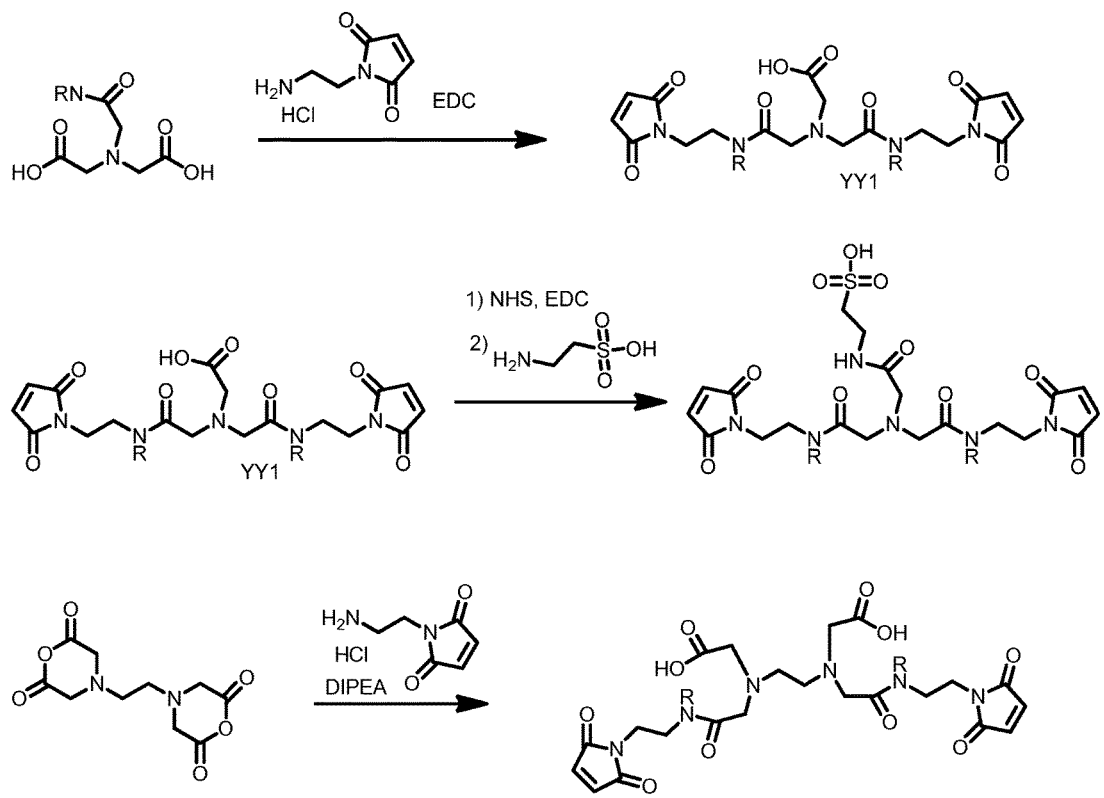
FIGS. 1-6 depict the synthetic schemes for preparing the linkers of the present invention.
Figure 2:
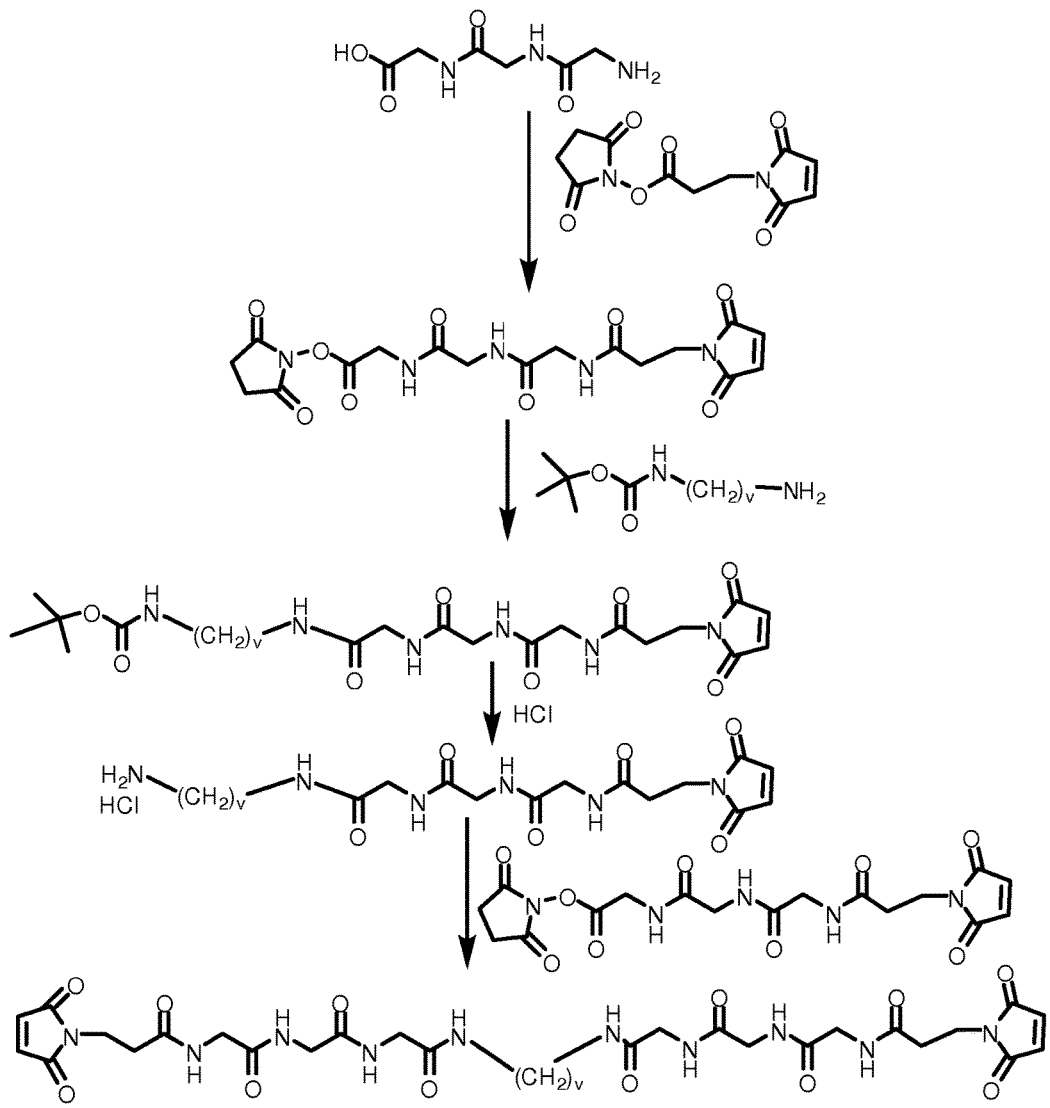
Figure 3:
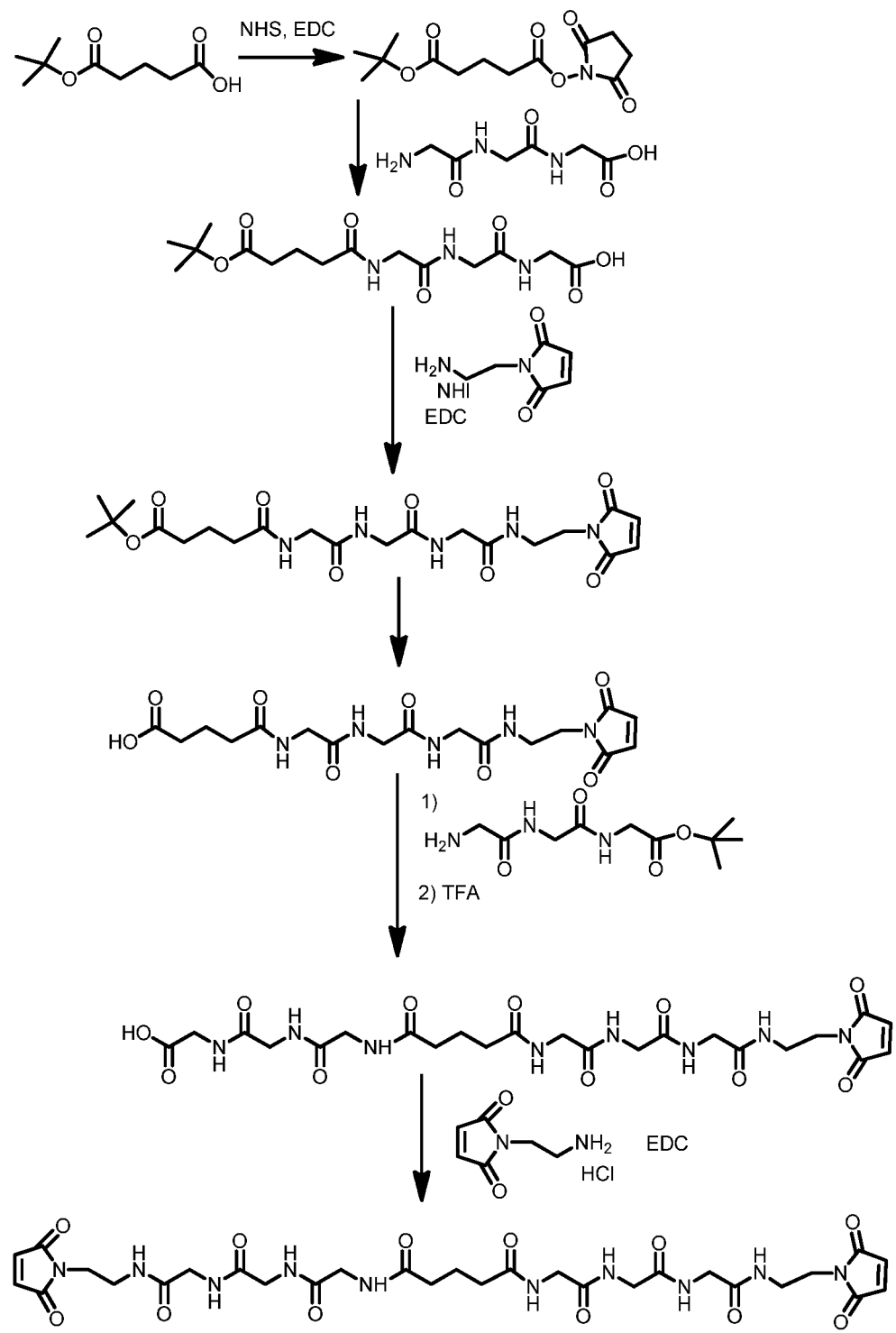
Figure 4:
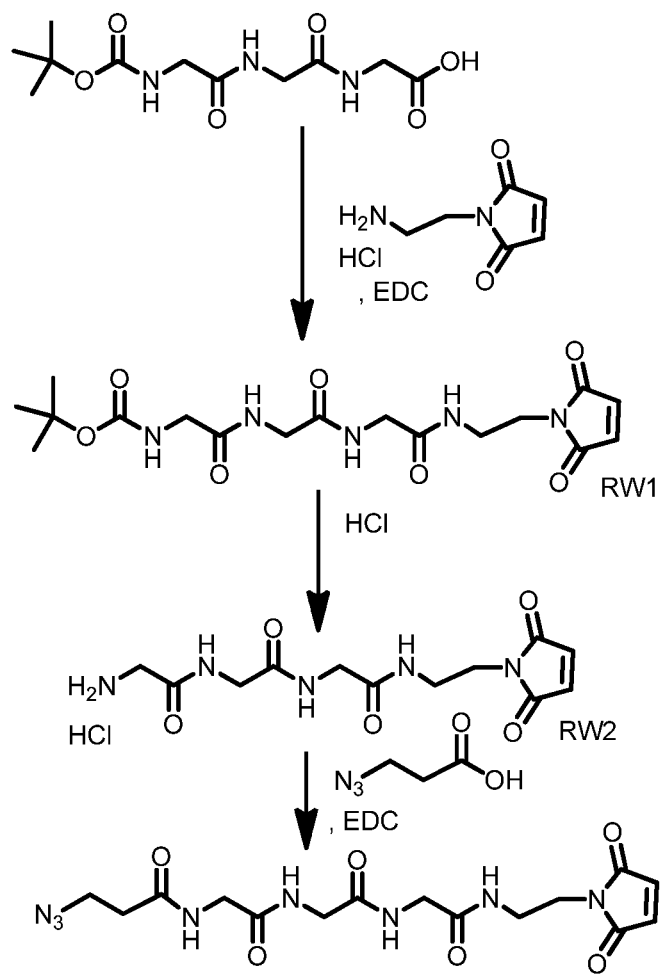
Figure 5:
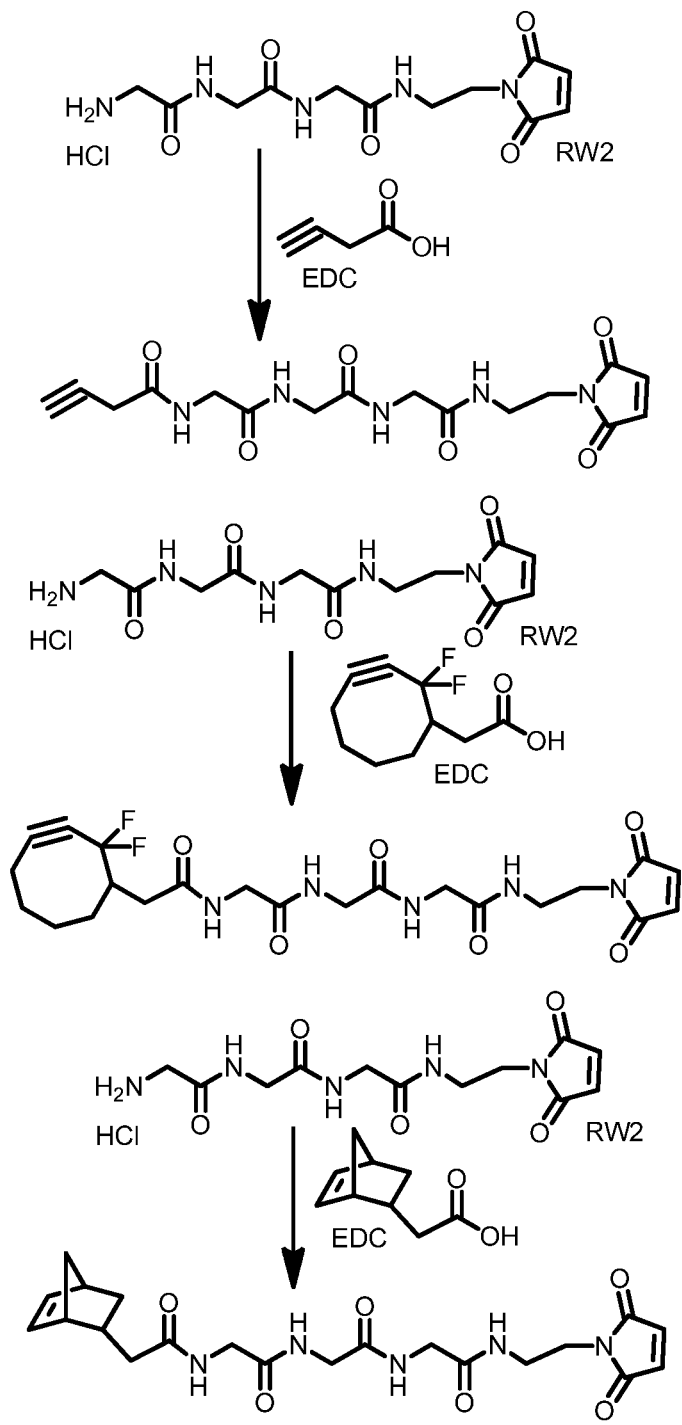
Figure 6:
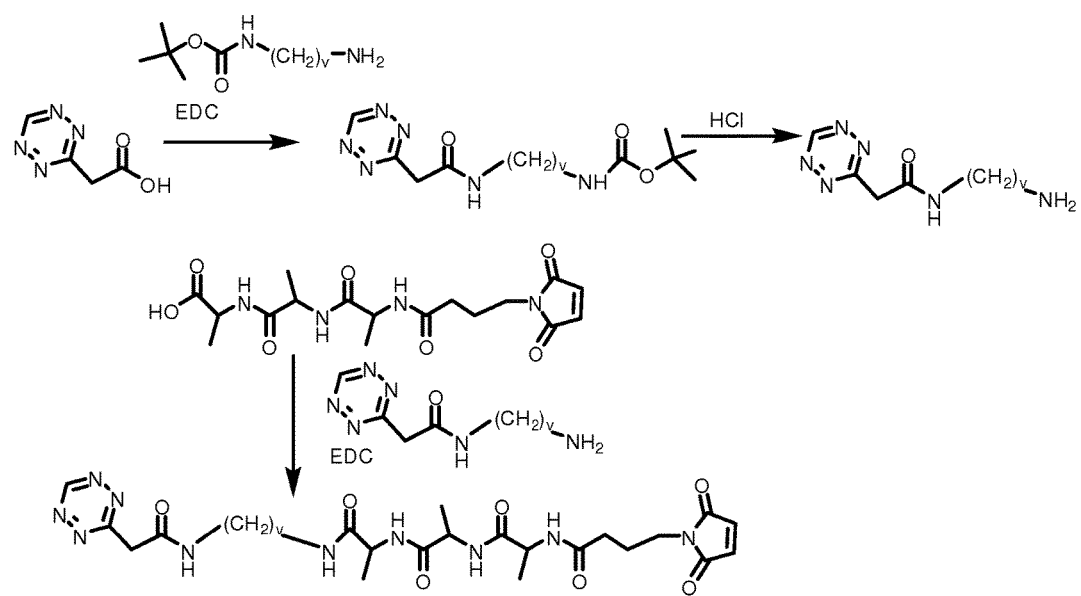

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Alkyl" as used herein refers to a saturated linear or branched-chain monovalent hydrocarbon radical of one to twenty carbon atoms. "Monovalent" means that alkyl has one point of attachment to the remainder of the molecule. Examples of alkyl groups include, but are not limited to, methyl, ethyl, 1-propyl, 2-propyl, 1-butyl, 2-methyl-1-propyl, —CH$_2$CH(CH$_3$)$_2$, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl group has one to ten carbon atoms. More preferably, the alkyl group has one to four carbon atoms.

"Alkylene" as used herein refers to a saturated linear or branched-chain divalent hydrocarbon radical of one to twenty carbon atoms, examples of which include, but are not limited to, those having the same core structures of the alkyl groups as exemplified above. "Divalent" means that the alkylene has two points of attachment to the remainder of the molecule. Preferably, the alkylene group has one to ten carbon atoms. More preferably, the alkylene group has one to four carbon atoms.

As used herein, an integer "between" x and y includes integers x and y unless otherwise specified to the contrary. For example, "an integer between 1 and 5" can be 1, 2, 3, 4, or 5.

The terms "cyclic alkyl" and "cycloalkyl" can be used interchangeably. They refer to a monovalent saturated carbocyclic ring radical. "Monovalent" means that cycloalkyl has one point of attachment to the remainder of the molecule. The saturated carbocyclic ring can be monocyclic or bicyclic (fused, bridged, or spiro bicyclic). Preferably, the cycloalkyl is 3 to 7 membered monocyclic ring radical. Bicyclic cycloalkyl having 7 to 12 atoms can be arranged, for example, as a bicyclo[4,5], [5,5], [5,6], or [6,6] system, and bicyclic cycloalkyl having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic cycloalkyl groups include, but are not limited to, cyclopropyl, cyclobutyl, cyclopentyl, cyclohexyl, cycloheptyl, cyclooctyl, cyclononyl, cyclodecyl, cycloundecyl, cyclododecyl, and the like. More preferably, the cycloalkyl is cyclohexyl.

"Cycloalkylene" as used herein refers to a divalent saturated carbocyclic ring radical having 3 to 12 carbon atoms as a monocyclic ring, or 7 to 12 carbon atoms as a bicyclic ring. "Divalent" means that the cycloalkylene has two points of attachment to the remainder of the molecule. Preferably, the cycloalkylene is a 3- to 7-membered monocyclic. Examples of cyclic alkylene groups include, but not limited to, those having the same core structures of the cylcolakyl groups as exemplified above. More preferably, the cycloalkylene group is cyclohexylene.

"Alkenyl" as used herein refers to aliphatic linear or branched-chain monovalent hydrocarbon radical of two to twenty carbon atoms with at least one carbon-carbon double bond, wherein the alkenyl radical includes radicals having "cis" and "trans" orientations, or by an alternative nomenclature, "E" and "Z" orientations. "Monovalent" means that alkenyl has one point of attachment to the remainder of the molecule. Examples include, but are not limited to, ethylenyl or vinyl (—CH=CH$_2$), allyl (—CH$_2$CH=CH$_2$), and the like. Preferably, the alkenyl has two to ten carbon atoms, also referred to as "C$_{2-10}$ alkenyl." More preferably, the alkenyl has two to four carbon atoms, also referred to as "C$_{2-4}$ alkenyl."

"Alkenylene" as used herein refers to aliphatic linear or branched-chain divalent hydrocarbon radical of two to twenty carbon atoms with at least one carbon-carbon double bond, wherein the alkenyl radical includes radicals having "cis" and "trans" orientations, or by an alternative nomenclature, "E" and "Z" orientations. "Divalent" means that the alkenylene has two points of attachment to the remainder of the molecule. Examples include, but are not limited to, ethylenylene or vinylene (—CH=CH—), allylene (—CH$_2$CH=CH—), and the like. Preferably, the alkenylene has two to ten carbon atoms, also referred to as "C$_{2-10}$ alkenylene." More preferably, the alkenylene has two to four carbon atoms, also referred to as "C$_{2-4}$ alkenylene."

The terms "cyclic alkenyl" and "cycloalkenyl" can be used interchangeably. They refer to a monovalent carbocyclic ring radical with at least one carbon-carbon double bond, having 3 to 12 carbon atoms as a monocyclic ring, or 7 to 12 carbon atoms as a bicyclic ring (fused, bridged, or spiro bicyclic). "Monovalent" means that cycloalkenyl has one point of attachment to the remainder of the molecule. Preferably, the cycloalkenyl is 3 to 7 membered monocyclic ring radical. Bicyclic cycloalkenyl having 7 to 12 atoms can be arranged, for example, as a bicyclo[4,5], [5,5], [5,6], or [6,6] system, and bicyclic cycloalkenyl having 9 or 10 ring atoms can be arranged as a bicyclo[5,6] or [6,6] system, or as bridged systems such as bicyclo[2.2.1]heptene, bicyclo[2.2.2]octene and bicyclo[3.2.2]nonene. Examples of the monocyclic alkenyl include, but are not limited to, cyclopropenyl, cyclobutenyl, cyclopentenyl, cyclohexenyl, cycloheptenyl, cyclooctenyl, cyclononenyl, cyclodecenyl, cycloundecenyl, cyclododecenyl, and the like. More preferably, the cycloalkenyl is cyclohexenyl.

"Cycloalkenylene" as used herein refers to a divalent unsaturated carbocyclic ring radical having 3 to 12 carbon atoms as a monocyclic ring, or 7 to 12 carbon atoms as a bicyclic ring. "Divalent" means that the cycloalkenylene has two points of attachment to the remainder of the molecule. Preferably, the cycloalkenylene is a 3- to 7-membered monocyclic. Examples of cyclic alkenylene include, but not limited to, those having the same core structures of the cylcolakyl groups as exemplified above. More preferably, the cycloalkenylene group is cyclohexenylene.

"Alkynyl" as used herein refers to aliphatic linear or branched-chain monovalent hydrocarbon radical of two to twenty carbon atoms with at least one carbon-carbon triple bond. "Monovalent" means that alkynyl has one point of attachment to the remainder of the molecule. Examples include, but are not limited to ethynyl, propynyl, 1-butynyl, 2-butynyl, 1-pentynyl, 2-pentynyl, 3-pentynyl, hexynyl, and the like. Preferably, the alkynyl has two to ten carbon atoms, also referred to as "$C_{2-10}$ alkynyl." More preferably, the alkynyl has two to four carbon atoms, also referred to as "$C_{2-4}$ alkynyl."

"Alkynylene" as used herein refers to an aliphatic linear or branched-chain divalent hydrocarbon radical of two to twenty carbon atoms with at least one carbon-carbon triple bond, examples of which include, but are not limited to, those having the same core structures of the alkynyl groups as exemplified above. "Divalent" means that the alkynylene has two points of attachment to the remainder of the molecule. Preferably, the alkynylene group has one to ten carbon atoms. More preferably, the alkynylene group has one to four carbon atoms.

The terms "cyclic alkynyl" and "cycloalkynyl" can be used interchangeably. They refer to a monovalent carbocyclic ring radical with at least one carbon-carbon triple bond, having 8 to 12 carbon atoms as a monocyclic ring, or 11 to 17 carbon atoms as a bicyclic ring (fused, bridged, or spiro bicyclic). "Monovalent" means that cycloalkynyl has one point of attachment to the remainder of the molecule. Preferably, the cycloalkynyl is 8-membered monocyclic ring radical.

"Cycloalkyne" as used herein refers carbocyclic ring having one or more triple bonds. It can be monocyclic, bicyclic or tricyclic; bicyclic and tricyclic can be bridged or fused. The carbocyclic ring optionally contains one or more double bonds and/or is optionally fused with one or more aromatic (e.g., phenyl ring) or heteroaromatic rings. Examples of cycloalkyne include, but are not limited to, those described in *J. Am. Chem. Soc.* (2012) 134:9199-9208; WO 2011/136645, US 2009/0068738, Lang K. et al., *J. Am. Chem. Soc.* (2012) 134:10317-10320, for example, cyclooctyne, monofluorocyclooctyne, difluorooctyne, DIFO, $DIFO_2$, $DIFO_3$, bicylo[6.1.0]non-4-yne, benzocyclooctyne, difluorobenzocyclooctyne, dibenzocyclooctyne, DIBO, and those described in Debets, M. F. et al., *Acc. Chem. Res.*, (2011) 44(9):805-815; and Gold B. et al., *J. Am. Chem. Soc.* (2013) 135(4):1558-1569. Preferably, cycloalkyne is cyclooctyne.

"Cycloalkynylene" as used herein refers to a divalent carbocyclic ring radical having at least one carbon-carbon triple bond. "Divalent" means that the cycloalkynylene has two points of attachment to the remainder of the molecule. Preferably, the cycloalkynylene is a 8-membered monocyclic.

"Heterocycloalkyne" as used herein refers to a heterocyclic ring having one or more triple bonds. Examples of heterocycloalkyne include, but are not limited to, dibenzoazacyclooctyne (DIBAC), biarylazacyclooctynone (BARAC), thiacyclooctyne, thiabenzocyclooctyne, thiacycloheptyne and tetramethylthiacycloheptyne.

"Strained cycloalkene" as used herein refers to carbocyclic ring having one or more double bonds, in which at least one of the double bonds forced by structural constraints has bond angles other than the typical 120° angle of non-strained alkenes. The strained cycloalkenes are more reactive than non-strained alkenes. Examples of strained cycloalkene include, but are not limited to, cyclooctene, norbornene and other cycloalkenes described in Debets, M. F. et al., *Acc. Chem. Res.* (2011) 44(9):805-815.

"Strained heterocycloalkene" as used herein refers to a heterocyclic ring having one or more double bonds, in which at least one of the double bonds forced by structural constraints has bond angles other than the typical 120° angle of non-strained heterocycloalkenes. The strained heterocycloalkenes are more reactive than non-strained heterocycloalkenes.

The term "aryl group" means an aromatic hydrocarbon ring system having six to fourteen carbon ring atoms. The term "aryl" may be used interchangeably with the terms "aryl ring" "aromatic ring," "aryl group" and "aromatic group." "Aryl group" also includes an aromatic hydrocarbon ring system fused to a non-aromatic carbocyclic ring system, such as a cycloalkyl group. Examples includes phenyl, naphthyl, anthracenyl, 1,2-dihydronaphthyl, 1,2,3,4-tetrahydronaphthyl, fluorenyl, indanyl, indenyl and the like. An aryl group is monovalent, i.e., has one point of attachment to the remainder of the molecule. A "substituted aryl group" is substituted at any one or more substitutable ring atom, which is a ring carbon atom bonded to a hydrogen."

"Arylene" as used herein refers to a divalent aryl group, i.e., an aryl group having two points of attachment to the remainder of the molecule. "Divalent" means that the arylene has two points of attachment to the remainder of the molecule. Both aryl and arylene groups are sometime represented herein by "Ar." Arylene is preferably phenylene.

Heteroaryl (used interchangeably with "heteroaromatic," "heteroaryl ring," "heteroaryl group," "heteroaromatic ring," and "heteroaromatic group") refers to aromatic ring systems having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings (e.g., bicyclic) in which a monocyclic heteroaromatic ring is fused to one or more other aromatic or heteroaromatic rings. As such, "5-14 membered heteroaryl" includes monocyclic, bicyclic or tricyclic ring systems. Heteroaryls are monovalent, meaning that there is one point of attachment to the remainder of the molecule.

"Monocyclic 5-6 membered heteroaryl" means a monocyclic aromatic ring system having five or six ring atoms selected from carbon and at least one (typically 1 to 3, more typically 1 or 2) heteroatoms (e.g., oxygen, nitrogen or sulfur). Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

"Heteroarylene" as used herein refers to a divalent heteroaryl, i.e., a heteroaryl with two points of attachment to the remainder of the molecule.

The terms "heterocycle," "heterocyclyl," heterocyclic and "heterocyclic ring" are used interchangeably herein and refer to a saturated or unsaturated non-aromatic 3-12 membered ring radical optionally containing one or more double bonds. It can be monocyclic, bicyclic, or tricyclic; bicyclic and tricyclic can be bridged or fused. The heterocycle contains 1 to 4 heteroatoms, which may be the same or different, selected from N, O or S. The heterocycle optionally contains one or more double bonds and/or is optionally fused with one or more aromatic (e.g., phenyl ring) or heteroaromatic rings. "3-7 membered monocyclic heterocycle" means a radical having from 3-7 atoms (including 1-3 heteroatoms) arranged in a monocyclic ring. The term "heterocycle" is intended to include all the possible isomeric forms. A heterocycle may be a monocycle having 3 to 7 ring members (e.g., 2 to 6 carbon atoms and 1 to 4 heteroatoms selected from N, O, P, and S) or a bicycle having 7 to 10 ring members (e.g., 4 to 9 carbon atoms and 1 to 6 heteroatoms selected from N, O, P, and S), for example: a bicyclo[4,5], [5,5], [5,6], or [6,6] system. Heterocycles are described in Paquette, Leo A., *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and *J. Am. Chem. Soc.* (1960) 82:5566.

Examples of heterocyclic rings include, but are not limited to, aziridinyl, pyrrolidinyl, tetrahydrofuranyl, dihydrofuranyl, tetrahydrothienyl, tetrahydropyranyl, dihydropyranyl, tetrahydrothiopyranyl, tetrahydropyrrolyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, isoindolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The heterocycle, heteroaryl, or heteroarylene groups may be carbon (carbon-linked) or nitrogen (nitrogen-linked) attached where such is possible. By way of example and not limitation, carbon bonded heterocycle, heteroaryl or heroarylene groups are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycle, heteroaryl, or heteroarylene groups are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole or isoindoline, position 4 of a morpholine, and position 9 of a carbazole, or O-carboline.

The heteroatoms present in heteroaryl, heteroarylene, or heterocyclcyl can include the oxidized forms such as NO, SO, and $SO_2$.

"Halogen" refers to F, Cl, Br or I.

If a group is described as being "optionally substituted," the group may be either (1) not substituted, or (2) substituted. If a carbon of a group is described as being optionally substituted with one or more of a list of substituents, one or more of the hydrogen atoms on the carbon (to the extent there are any) may separately and/or together be replaced with an independently selected optional substituent.

Suitable substituents for an alkyl, alkenyl, alkynyl, cycloalkyl, aryl, heteroaryl, heterocycle, alkylene, alkenylene, alkynylene, cycloalkene, heterocycloalkene, cycloalkyne, heterocycloalkyne, cycloalkylene arylene, and heterarylene are those which do not significantly adversely affect the biological activity of the conjugate. Unless otherwise specified, exemplary substituents for these groups include linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$_{100}$, NR$_{101}$R$_{102}$, —NO$_2$, —NR$_{101}$COR$_{102}$, —SR$_{100}$, a sulfoxide represented by —SOR$_{101}$, a sulfone represented by —SO$_2$R$_{101}$, a sulfonate —SO$_3$M, a sulfate —OSO$_3$M, a sulfonamide represented by —SO$_2$NR$_{101}$R$_{102}$, cyano, an azido, —COR$_{101}$, —OCOR$_{101}$, —OCONR$_{101}$R$_{102}$ and a polyethylene glycol unit (—OCH$_2$CH$_2$)$_n$R$_{101}$ wherein M is H or a cation (such as Na$^+$ or K$^+$); R$_{101}$, R$_{102}$ and R$_{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$_{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$_{104}$ is H or a linear or branched alkyl having 1 to 4 carbon atoms, wherein the alkyl, alkenyl, alkynyl, aryl, heteroaryl and heterocyclcyl in the groups represented by R$_{100}$, R$_{101}$, R$_{102}$, R$_{103}$ and R$_{104}$ are optionally substituted with one or more (e.g., 2, 3, 4, 5, 6 or more) substituents independently selected from halogen, —OH, —CN, —NO$_2$, and unsubstituted linear or branched alkyl having 1 to 4 carbon atoms. Preferably, the substituent for the optionally substituted alkyl, alkylene, cycloalkylene, arylene, and heteroarylene described above is selected from the group consisting of halogen, —CN, —NR$_{101}$R$_{102}$, —CF$_3$, —OR$_{100}$, aryl, heteroaryl, heterocyclyl, —SR$_{101}$, —SOR$_{101}$, —SO$_2$R$_{101}$, and —SO$_3$M. Alternatively, the suitable substituent is selected from the group consisting of -halogen, —OH, —NO$_2$, —CN, C$_{1-4}$ alkyl, —OR$_{100}$, NR$_{101}$R$_{102}$, —NR$_{101}$COR$_{102}$, —SR$_{100}$, —SO$_2$R$_{101}$, —SO$_2$NR$_{101}$R$_{102}$, —COR$_{101}$, —OCOR$_{101}$, and —OCONR$_{101}$R$_{102}$, wherein R$_{100}$, R$_{101}$, and R$_{102}$ are each independently —H or C$_{1-4}$ alkyl.

The term "ionizable group" refers to a functional group that can be converted to a charged group by protonation with an acid or deprotonation with a base. Examples of the ionizable groups include —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'CO$_2$H, —NR$_{11}$R$_{12}$, or —Z'—NR$_{11}$R$_{12}$, R$_{11}$ and R$_{12}$, for each occurrence, are independently H or an optionally substituted alkyl; and Z' includes an optionally substituted alkylene, an optionally substituted cycloalkylene or an optionally substituted phenylene. In certain embodiments, Z' is alkylene.

The term "charged substituent" refers to a substituent that is either positively or negatively charged. The charge in such a substituent is not removable by treatment with a base or an acid and thus permanent. Examples of the charged substituents include, but not limited to, —N$^+$R$_{13}$R$_{14}$R$_{15}$ and —Z'—N$^+$R$_{13}$R$_{14}$R$_{15}$, in which R$_{13}$ to R$_{15}$ are each independently an optionally substituted alkyl; and Z' includes an optionally substituted alkylene, an optionally substituted cycloalkylene or an optionally substituted phenylene. In certain embodiments, Z' is alkylene.

Charged substituents may contain a counter ion. For positive charged substituents, the counter ion is negative and can be represented by "X$^-$," e.g., as —N$^+$R$_{13}$R$_{14}$R$_{15}$X$^-$ and —Z'—N$^+$R$_{13}$R$_{14}$R$_{15}$X$^-$. The counter ions for the positively charged substituents are anions (preferably pharmaceutically acceptable anions), which include, but are not limited to, acetate, benzenesulfonate, benzoate, bicarbonate, bitartrate, bromide, calcium edetate, camsylate, carbonate, chloride, bromide, citrate, dihydrochloride, edetate, edisylate, estolate, esylate, fumarate, glyceptate, gluconate, glutamate, glycollylarsanilate, hexylresorcinate, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide. Preferably, the counter ions for the positively charged substituents are chloride, bromide, sulfate, and phosphate.

The counter ions for the negatively charged substituents include, but are not limited to, an alkali metal ion (e.g., sodium and potassium), an alkaline earth metal ion (e.g., calcium and magnesium), aluminum ion, ammonium, protonated trialkyl amines (e.g., trimethylamine and triethylamine), a tetraalkyl ammonium (e.g., tetra methyl ammonium, and tetrabutyl ammonium), and a protonated heteroaromatic group (e.g., pyridine, pyrimidine, triazines, tetrazines). Preferably, the counter ions for the negatively charged substituents are sodium, potassium, lithium, protonated triethyl amine, protonated pyridiene. Most preferably, the counter ions for the negatively charged substituents are sodium and potassium. The counter ions for both the negatively and positively charged substituents may be removed or replaced in subsequent purification steps.

"Amino acid" as used herein, including the residue represented by variable "XX" described above, refers to naturally occurring amino acids, unnatural amino acids, amino acid analogs, or amino acid mimetics that function in a manner similar to the naturally occurring amino acids.

The term "Naturally occurring amino acids" as used herein refers to those twenty L-amino acids encoded by the universal genetic codes and appearing in proteins or peptides, as well as selenocysteine and pyrrolysine that are incorporated into proteins by distinctive biosynthetic mechanisms. They include Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, selenocysteine and pyrrolysine. The term "Naturally occurring amino acids" also refers to those produced by the body, but are not encoded by the universal genetic codes, such as β-Alanine, Ornithine, and citrulline. The term "Naturally occurring amino acids" further includes those naturally occurring L-amino acids that are later modified (e.g., via post-translational modification by enzymes) in the body, such as hydroxyproline, γ-carboxyglutamate, and O-phosphoserine.

The term "unnatural amino acids" as used herein is intended to include the "D" stereochemical form of the naturally occurring amino acids described above. It is further understood that the term "unnatural amino acids" includes homologues of the natural L-amino acids or their D isomers, and synthetically modified forms of the natural L-amino acids or their D isomers. The synthetically modified forms include, but are not limited to, amino acids having side chains shortened or lengthened by up to two carbon atoms, amino acids comprising optionally substituted aryl groups, and amino acids comprised halogenated groups, preferably halogenated alkyl and aryl groups and also N substituted amino acids e.g. N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, N-methyl-selenocysteine, and N-methyl-pyrrolysine, each including an L or D isomer.

The term "amino acid analogs" as used herein refers to compounds that have the same basic chemical structure as a naturally occurring amino acid, i.e., an a carbon that is bound to a hydrogen, a carboxyl group, an amino group, and an R group. They include 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, homoserine, norleucine, cysteine sulfonic acid, cysteine sulfinic acid, methionine sulfoxide, and methionine methyl sulfonium. Such analogs may have modified R groups (e.g., norleucine) or modified peptide backbones, but retain the same basic chemical structure as a naturally occurring amino acid. Amino acid analogs also include D isomers of the above-referenced L-isomers.

The term "amino acid mimetics" as used herein refers to chemical compounds that have a structure that is different from the general chemical structure of an amino acid, but functions in a manner similar to a naturally occurring amino acid.

"Peptide" as used herein, including the peptide represented by variable P or P' when the variable is [XX]$_{2-10}$, refers to short polymers of amino acid monomers linked by peptide bonds, the covalent chemical bonds formed between two amino acid monomers when the carboxyl group of N-terminal monomer reacts with the amino group of the C-terminal monomer. The preferred length of the peptide is two to ten amino acids as described above.

Any one of the peptides described herein can be connected to the rest of the molecules in either direction. For example, when AA1, AA2, and AA3 each represent an amino acid (naturally-occurring, or unnatural), "AA1-AA2-AA3 in either direction" refers to the tripeptide N-AA1-AA2-AA3-C), and the tripeptide N-AA3-AA2-AA1-C).

In certain embodiments, variable P or P' is an amino acid represented by [XX]$_1$ or a peptide represented by [XX]$_{2-10}$, in which each XX is the residue of an independently selected amino acid selected from the group consisting of: Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, selenocysteine, and pyrrolysine, N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, N-methyl-selenocysteine, N-methyl-pyrrolysine, hydroxyproline, γ-carboxyglutamate, selinocysteine, O-phosphoserine, homoserine, norleucine, methionine sulfoxide, methionine methyl sulfonium, citrulline, Ornithine, cysteine sulfonic acid, cysteine sulfinic acid, 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, and β-alanine, each independently as an L or D isomer. In another alternative, each XX is the residue of an independently selected amino acid selected from glycine or alanine, each independently as an L or D isomer.

In certain embodiments, the peptide represented by variable P or P' is cleavable by a protease. In one embodiment, the protease is a protease expressed in tumor tissue. In another embodiment, the protease is a lysosomal protease.

The term "peptide cleavable by a protease" as used herein refers to peptides containing a cleavage recognition sequence of a protease. A cleavage recognition sequence for a protease is an amino acid sequence recognized by the protease during proteolytic cleavage. Many protease cleavage sites are known in the art, and these and other cleavage sites can be included in the linker moiety. See, e.g., Matayoshi et al., *Science* 247:954 (1990); Dunn et al., *Meth. Enzymol.* 241:254 (1994); Seidah et al., *Meth. Enzymol.* 244:175 (1994); Thornberry, *Meth. Enzymol.* 244:615 (1994); Weber et al., *Meth. Enzymol.* 244:595 (1994); Smith et al., *Meth. Enzymol.* 244:412 (1994); Bouvier et al., *Meth. Enzymol.* 248: 614(1995), Hardy et al, in *AMYLOID PROTEIN PRECURSOR IN DEVELOPMENT, AGING, AND ALZHEIMER'S DISEASE*, Ed. Masters et al., pp. 190-198 (1994).

In one embodiment, the peptide sequence is chosen based on its ability to be cleaved by a tumor-associated protease, e.g., a protease that is found on the surface of a cancerous cell or extracellularly in the vicinity of tumor cells. The examples of such proteases include thimet oligopeptidase (TOP), CD10 (neprilysin), a matrix metalloprotease (such as MMP2 or MMP9), a type II transmebrane serine protease (such as Hepsin, testisin, TMPRSS4 or matriptase/MT-SP1), legumain and enzymes described in the following reference: *Current Topics in Developmental Biology: Cell Surface Proteases*, vol. 54 Zucker S. 2003, Boston, Mass. The ability of a peptide to be cleaved by tumor-associated protease can be tested using in vitro protease cleavage assays known in the art.

In another embodiment, the peptide sequence is chosen based on its ability to be cleaved by a lysosomal protease, which include cathepsins B, C, D, H, L and S, and furin. Preferably, the peptide sequence is capable of being cleaved by an appropriate isolated protease in vitro, which can be tested using in vitro protease cleavage assays known in the art.

In certain embodiments, the peptide is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu, Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala, Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly. In another alternative, the peptide is selected from the group consisting of Gly-Gly-Gly, Ala-Ala-Ala, D-Ala-Ala-Ala, Ala-D-Ala-Ala, Ala-Val-Ala, and β-Ala-Gly-Gly-Gly. In a related embodiment, any of the peptide sequences herein above may be in either direction, as defined above.

An amino acid or peptide can be attached to a linker/spacer or a cell binding agent through the terminal amine or terminal carboxylic acid of the amino acid or peptide. The amino acid can also be attached to a linker/spacer or a cell-binding agent through a side chain reactive group, including, but not restricted to, the thiol group of cysteine, the epsilon amine of lysine, and the side chain hydroxyls of serine or threonine.

Amino acids and peptides may be protected by blocking groups. A blocking group is an atom or a chemical moiety that protects an amino acid or a peptide (e.g., the N-terminus) from undesired reactions and can be used during the synthesis of a drug-ligand conjugate. It should remain attached to the amino acid or peptide (e.g., to the N-terminus) throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, methyl esters, tert-butyl esters, 9-fluorenylmethyl carbamate (Fmoc) and carbobenzoxy (Cbz).

The term "blocking group" or "protecting group" refers to a substituent that is commonly employed to block or protect a particular functionality while reacting other functional groups on the compound, a derivative thereof, or a conjugate thereof. For example, an "amine-protecting group" is a substituent attached to an amino group that blocks or protects the amino functionality in the compound. Such groups are well known in the art (see for example P. Wuts and T. Greene, 2007, *Protective Groups in Organic Synthesis*, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, *Protective Groups in Organic Synthesis*, John Wiley & Sons, New York, 2007.

The term "reactive ester" as used herein refers to an ester group having a leaving group that is readily displaced by an amine group. Examples of a reactive ester, include, but are not limited to, N-hydroxysuccinimide ester, N-hydroxysulfosuccinimide ester, nitrophenyl (e.g., 2 or 4-nitrophenyl) ester, dinitrophenyl (e.g., 2,4-dinitrophenyl) ester, sulfotetraflurophenyl (e.g., 4-sulfo-2,3,5,6-tetrafluorophenyl)ester and pentafluorophenyl ester.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 (the entire teachings of which are incorporated herein by reference), and also see C. Zahnd et al., *Cancer Res.* (2010) 70:1595-1605; Zahnd et al., *J. Biol. Chem.* (2006) 281(46): 35167-35175; and Binz, H. K., Amstutz, P. & Pluckthun, A., *Nature Biotechnology* (2005) 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide. As used herein, "AVIBODY™" cell binding agents (or "AVIBODY CBA" in short) includes a family of proteins as cell binding agents that specifically bind desired targets. As is well known, antibodies bind such desired targets through "Target Binding Regions" (TBRs) or Fv domains. AVIBODY™ CBA typically contains two, three, or four TBRs more commonly known as Dia-, Tria- and Tetra-bodies. These TBRs/Fv domains are linked together by fusing the Fv V-domains together in a "head to tail" orientation, forming stable, specific, and highly customizable multimeric antibody-like proteins as AVIBODY™ CBA. See, for example, U.S. Publication Nos. 2008/0152586 and 2012/0171115 for details, the entire teachings of which are incorporated herein by reference.

The term "cell binding agent" as used herein refers to a compound that can bind a cell (e.g., on a cell-surface ligand) or bind a ligand associated with or proximate to the cell, either in a specific or non-specific manner. In certain embodiments, binding to the cell or a ligand on or near the cell is specific. The cell-binding agent may be of any kind presently known, or that become known and includes peptides and non-peptides.

In certain embodiments, the cell-binding agents are proteins or polypeptides, or compounds comprising proteins or polypeptides, including both antibody and non-antibody proteins or polypeptides. Preferably, the cell-binding agents (e.g., proteins or polypeptides) comprise one or more Cys residues. The side chain —SH group of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains). Alternatively or in addition, the cell-binding agents (e.g., proteins or polypeptides) comprise one or more amino acids that are modified to contain a reactive functional group that can react with the linkers (e.g., Formula (VI'), (VI), (VII'), (VII), (XI') or (XI)) or cytotoxic compounds (e.g., Formula (IV'), (IV), (V'), (V), (X') or (X)) of the invention. For example, the reactive functional group is —SH, —C(=O)—, —NHNH$_2$, —N$_3$, -alkyne, tetrazine, strained cycloalkene or strained heterocycloalkene, dithioester, or diene (see, for example, Vu Hong et al., *Bioconjugate Chem.* (2010) 21(10):1912-1916; Glassner, M. et al., *J. Am. Chem. Soc.* (2012) 134:7274-7277; Hansell, C. F. et al., *J. Am. Chem. Soc.* (2011) 133:13828-13831; Neal K. Devaraj, *Synlett* (2012) 23(15):2147-2152; Chenoweth, K. et al., *Organic & Biomolecular Chemistry* (2009) (24):5255; Jewett, J. C. et al., *J. Am. Chem. Soc.* (2010) 132(11):3688-3690; Seitchik J. L. et al., *J. Am. Chem. Soc.* (2012) 134(6):2898-2901; and Sletten E. M. et al., *Angew Chem. Int. Ed. Engl.* (2009) 48(38):6974-6998). The reactive functional group can be introduced into the cell-binding agent through any chemical or enzymatic method known in the art. See, for example, Davis L. K. et al., *J. Am. Chem. Soc.* (2012) 134:10317-10320; Boeggeman E, et al., *Bioconjug Chem.* (2009 Jun. 20) (6):1228-36; Stan A C, et al., *Cancer Res.* (1999 Jan. 1) 59(1):115-21; Mahal, L. K. et al., *Science* (1997) 276:1125-1128; Saxon, E., and Bertozzi, C. R., *Science* (2000) 287:2007-2010; Hang, H. C. et al., *Proc. Natl. Acad. Sci. USA* (2003) 100:14846-14851; Vocadlo, D. J. et al., *Proc. Natl. Acad. Sci. USA* (2003) 100:9116-9121; Prescher, J. A. et al., *Nature* (2004) 430:873-877; Dube, D. H. et al., *Proc. Natl. Acad. Sci. USA* (2006) 103:4819-4824; Jeger S, et al., *Angew Chem Int Ed Engl.* (2010 Dec. 17) 49(51):9995-9997; and Lang K. et al., *J. Am. Chem. Soc.* (2012) 134:10317-10320.

Cell-binding agent can also be peptides derived from phage display (see, for example, Wang et al., *Proc. Natl. Acad. Sci. USA* (2011) 108(17):6909-6914) or peptide library techniques (see, for example, Dane et al., *Mol. Cancer. Ther.* (2009) 8(5):1312-1318).

In one embodiment, one or more reactive functional groups that are capable of reacting with the linkers (Formula (VI'), (VI), (VII'), (VII), (XI') or (XI)) or the cytotoxic compounds (Formula (IV'), (IV), (V'), (V), (X') or (X)) of the present invention can be introduced into the cell-binding agent by any methods known in the art. For example, a terminal amine group on the cell-binding agent can be converted to a carbonyl group through transamination reaction (see, for example, US 2010/0099649; *Angew. Chem. Int. Ed.,* 45(32):5307 (2006); *Chem. Biol.,* 2(4):247 (2007); *J. Am. Chem. Soc.,* 130(35):11762, 2008). Alternatively, the cell-binding agent can be engineered to include one or more free cysteine residues (i.e., cysteine residues having a free —SH group that can react with the linkers or the cytotoxic compounds of the present invention) according to any methods known in the art (see, for example, U.S. Pat. No. 7,521,541). In another alternative, thiol groups (—SH) can be generated by controlled reduction of interchain disulfides of antibodies, followed by treatment with a cytotoxic agent bearing a maleimido group, as described in U.S. Pat. Nos. 7,659,241, 8,309,300, 7,855,275, 7,723,485 and 7,521,541. For example, partial or complete reduction of interchain disulfides followed by conjugation with a cytotoxic agent bearing a maleimido group can yield a conjugate with 2, 3, 4, 5, 6, 7 or 8 cytotoxic agent molecules covalently linked to each antibody molecule. Alternatively, conjugates having 2, 3, 4, 5, 6, particularly 4 or 6, cytotoxic agent molecules covalently attached to each antibody molecule can be prepared by complete reduction of interchain disulfide of the antibody followed by partial re-oxidation and then conjugation with cytotoxic agent. In another alternative, these conjugates can be prepared by partial or complete reduction of interchain disulfides of the antibody followed by conjugation with cytotoxic agent and then partial re-oxidation. Thiol groups can also be introduced into the cell-binding agent (e.g., antibodies) by reaction with a crosslinking agent such as 2-iminothiolane (see for example Goff and Carroll, *Bioconjugate Chem.* (1990) 1(6):381-386) followed by reaction with a cytotoxic agent bearing a maleimido group (e.g., compounds of Formula (IV'), (IV), (V'), (V), (X') or (X)) to provide a conjugate. All these methods for introducing reactive functional groups are applicable for cell-binding agents that are not antibodies, which, for example, include Centyrin, DARPin, Avibody, adnectin or antibody fragment, such as minibodies, diabodies, tribodies, tetrabodies, nanobodies, probodies, domain bodies or unibodies.

In one embodiment, when the cell-binding agent is a Centyrin, one or more reactive functional groups (e.g., a cysteine having a free thiol group) can be introduced according to methods described in US 2010/0255056, US 2010/0216708 and US 2011/0274623.

In another embodiment, the cell-binding agent is a DARPin and it can be prepared according to methods described in US Publication Nos. 2004/0132028, 2009/0082274, 2011/0118146, and 2011/0224100, WO 02/20565 and WO 06/083275. Preferably, DARPin comprises one or more cysteine residues at specific positions that do not interfere with antigen binding. Such cysteine residue can react with the linkers (e.g., Formula (VI'), (VI), (VII'), (VII), (XI') or (XI)) or the cytotoxic compounds (e.g., Formula (IV'), (IV), (V'), (V), (X') or (X)) of the present invention.

In yet another embodiment, Avibodies having one or more cysteine residues can be prepared according to methods described in US 2008/0139791 and US 2012/0171115.

The Cys side chain —SH groups or the other reactive functional groups described above may be covalently linked to the linkers (e.g., linkers of Formula (VI'), (VI), (VII'), (VII), (XI') or (XI)), which are in turn linked to the cytotoxic compounds, thus conjugating the cell-binding agents to the cytotoxic compounds to yield the conjugates of the invention (e.g., conjugates of Formula (I'), (I), (III'), (III), (IX') or (IX)). Alternatively, the Cys side chain —SH groups or the reactive functional groups may be covalently linked to the cytotoxic compounds of the invention having linkers bound thereto (e.g., cytotoxic compounds of Formula (IV'), (IV), (V'), (V), (X') or (X)). Each protein-based cell-binding agents may contain multiple Cys side chain —SH groups and/or the reactive functional groups available for linking the compounds of the invention.

Examples of the cell binding agents include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon, a lymphokine (e.g., IL-2, IL-3, IL-4, and IL-6), a hormone (e.g., insulin, thyrotropin releasing hormone, melanocyte-stimulating hormone, and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al., *J. Biol. Chem.* (1985) 260:932-937, incorporated herein by reference), a Centyrin (a protein scaffold based on a consensus sequence of fibronectin type III (FN3) repeats; see U.S. Patent Publication Nos. 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), and other cell-binding molecules or substances.

In certain embodiments, the cell-binding agent is an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule. Alternatively, the cell-binding agent is a monoclonal antibody, a single chain monoclonal antibody, or a monoclonal antibody fragment that specifically binds to a target cell.

In certain embodiments, the cell-binding agent is a bispecific antibody, an ankyrin repeat protein, a Centyrin, or an Avibody.

"Antibody fragment" refers to Fab, Fab', and F(ab')$_2$, Fv, minibodies, diabodies, tribodies, tetrabodies, nanobodies, probodies, domain bodies, unibodies, and the like (Parham, *J. Immunol.* 131:2895-2902 (1983); Spring et al., *J. Immunol.* 113:470-478 (1974); Nisonoff et al., *Arch. Biochem. Biophys.* 89:230-244 (1960), Kim et al., *Mol, Cancer Ther.*, 7 2486-2497 (2008), Carter, *Nature Revs.*, 6:343-357 (2006), R. Kontermann & S. Dubel, 2001 *Antibody Engineering*, Springer-Verlag, Heidelberg-New York).

In certain embodiments, the cell-binding agent is a minibody, a diabody, a tribody, a tetrabody, a nanobody, a probody, a domain body, or an unibody.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Selection of the appropriate cell-binding agent is a matter of choice that depends upon the particular cell population that is to be targeted, but in general human monoclonal antibodies are preferred if an appropriate one is available. For example, the monoclonal antibody MY9 is a murine IgG$_1$ antibody that binds specifically to the CD33 Antigen (J. D. Griffin et al., *Leukemia Res.* (1984) 8:521) and can be used if the target cells express CD33 as in the disease of acute myelogenous leukemia (AML).

In one embodiment, the cell-binding agent is a resurfaced antibody, a resurfaced single chain antibody, or a resurfaced antibody fragment.

In another embodiment, the cell-binding agent is a humanized antibody, a humanized single chain antibody, or a humanized antibody fragment. In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Provisional Application Nos. 61/307,797, 61/346,595, and 61/413,172 and U.S. application Ser. No. 13/033,723 (published as US 2012/0009181 A1). The teachings of all these applications are incorporated herein by reference in its entirety.

In certain embodiments, the cell-binding agent is an antigen-binding portion of a monoclonal antibody, sharing sequences critical for antigen-binding with an antibody disclosed herein, such as huMy9-6 or its related antibodies described in U.S. Pat. Nos. 7,342,110 and 7,557,189, incorporated herein by reference. These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In an alternative, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the K$_d$ and/or k$_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

Specific exemplary antigens or ligands include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, and CD152), one or more tumor-associated antigens or cell-surface receptors (see US Publication No. 20080171040 or US Publication No. 20080305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

For example, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

The term "salt" as used herein refers to organic or inorganic salts of a compound of the invention. Preferably, a salt is a pharmaceutically acceptable salt. Other non-pharmaceutically acceptable salts are also included in the present invention. The salts include salts, formed by reacting a compound of the invention, which comprises a basic group, with an inorganic acid or organic acid (such as a carboxylic acid), and salts, formed by reacting a compound of the invention, which comprises an acidic group, with an inorganic base or organic base (such as an amine). Exemplary salts include those pharmaceutically acceptable salts described immediately below.

The term "pharmaceutically acceptable salt" as used herein refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention contains one or more basic moieties, desired salts (e.g., pharmaceutically acceptable salts) may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention contains one or more acidic moieties, desired salts (e.g., pharmaceutically acceptable salts) may be prepared by any suitable method, for example, treatment of the free acid with an inorganic, such as an alkali metal hydroxide or alkaline earth metal hydroxide, organic base, such as an amine (primary, secondary or tertiary), or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells. Examples of cancer include, but are not limited to, carcinoma, lymphoma, blastoma, sarcoma, and leukemia or lymphoid malignancies. More particular examples of such cancers include skin cancer (e.g., melanoma), Merkel cell carcinoma, squamous cell cancer (e.g., epithelial squamous cell cancer), lung cancer (e.g., small-cell lung cancer, non-small cell lung cancer, adenocarcinoma of the lung, and squamous carcinoma of the lung), cancer of the peritoneum, hepatocellular cancer, gastric or stomach cancer (e.g., gastrointestinal cancer), pancreatic cancer, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, testicular cancer, vulval cancer, thyroid cancer, hepatic carcinoma, anal carcinoma, penile carcinoma, acute leukemia, head and neck cancer, brain cancer (e.g., glioblastoma and neuroblastoma), cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

The term "therapeutic agent" encompasses both a biological agent such as an antibody, a peptide, a protein, an enzyme or a chemotherapeutic agent.

The term "Chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

Chemotherapeutic agents may also include any of the generic drugs or biosimilars of the brand-name drugs referenced herein, or improvements thereof, including improved formulations, delivery means (sustained release, bioadhesive coating, targeted delivery etc.), and dosage forms.

The term "viral infection" refers to the invasion of a host organism's bodily tissues by disease-causing viruses. Examples of the viral infections include CMV infection, HIV infection and AIDS.

The term "parasite infection" refers to the invasion of a host organism's bodily tissues by disease-causing parasites. Examples of the parasite infections include giardiasis, amoebiasis, and schistosomiasis.

The phrase "pharmaceutically acceptable" indicates that the substance or composition must be compatible chemically and/or toxicologically, with the other ingredients comprising a formulation, and/or the mammal being treated therewith.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cell Binding Agent-Drug Moiety Conjugates

The present invention provides a conjugate represented by Formula (I'), (I), (III'), (III), (IX') or (IX) as described in the first or second embodiment and their alternative embodiments above. In addition, twenty-eight specific embodiments for the conjugate are further described below in this conjugate section.

In a first specific embodiment, the conjugate is represented by the following formula, or a pharmaceutically acceptable salt thereof:

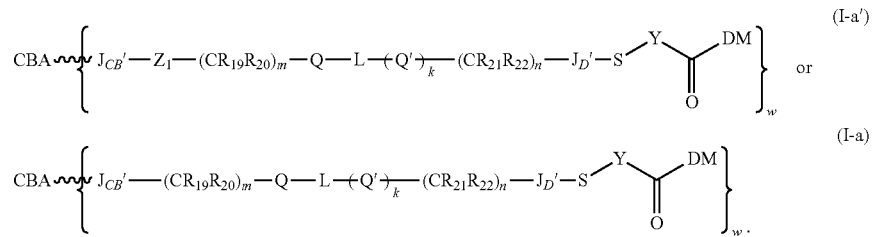

In Formula (I-a') or (I-a) above, $R_{19}$ to $R_{22}$, for each occurrence, are independently H or an optionally substituted alkyl; m and n are each independently 0 to 10; and the remainder of the variables are as defined in the first embodiment or each of its alternative embodiments. Preferably, $R_{19}$ to $R_{22}$ are all H. Alternatively, $R_{19}$ to $R_{22}$ are all H; and m and n are 2. In a second specific embodiment, in Formula (I'), (I), (I-a') or (I-a), the ionizable group is —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, and the charged group is —$N^+R_{23}R_{24}R_{25}X^-$, or —Z'—$N^+R_{23}R_{24}R_{25}X^-$; Z' is an optionally substituted alkylene, an optionally substituted cycloalkylene, or an optionally substituted phenylene; $R_{23}$ to $R_{25}$ are each independently an optionally substituted alkyl; and $X^-$ is a pharmaceutically acceptable anion. In this second specific embodiment, the remainder of the variables are as defined in the first embodiment or each of its alternative embodiments, or its first specific embodiment.

In a third specific embodiment, within the ionizable group or the charged substituent described in the preceding paragraph immediately above, variable Z' is alkylene, and the remainder of the variables are as defined in the first embodiment or each of its alternative embodiments, or its first or second specific embodiment.

In a fourth specific embodiment, in Formula (I'), (I), (I-a') or (I-a), V is H or —$CH_2CH_2SO_3H$ or a pharmaceutically acceptable salt thereof; and the remainder of the variables are as defined in the first embodiment or each of its alternative embodiments or its first specific embodiment.

In a fifth specific embodiment, the conjugate is represented by the following formula, or a pharmaceutically acceptable salt thereof:

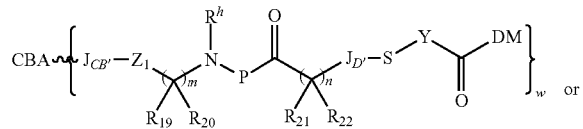
(I-b')

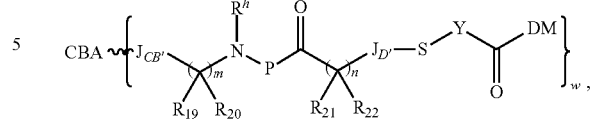
(I-b)

in which the variables are as defined in the first embodiment or each of its alternative embodiments, or its first specific embodiment.

In a sixth specific embodiment, the conjugate is represented by the following formula, or a pharmaceutically acceptable salt thereof:

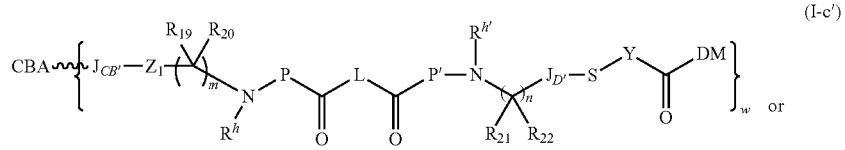
(I-c')

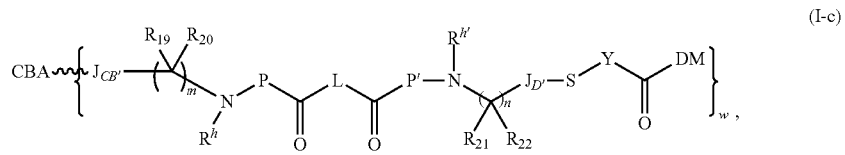
(I-c)

in which the variables are as defined in the first embodiment or each of its alternative embodiments, or its first, second, third, or fourth specific embodiment. Preferably, P and P' are the same.

In a seventh specific embodiment, in Formula (I'), (I), (I-a'), (I-a), (I-c') or (I-c), L is —$(CR_7R_8)_q$—$N(R^g)$—$(CR_9R_{10})_r$— or —$(CR_{11}R_{12})_s$—$N(R^g)$—$(CR_{13}R_{14})_t$—$N(R^{g'})$—$(CR_{15}R_{16})_u$—; and the remainder of the variables are as defined in the first embodiment or each of its alternative embodiments or its first, second, third, fourth, or sixth specific embodiment.

In an eighth specific embodiment, the conjugate is represented by a formula selected from:

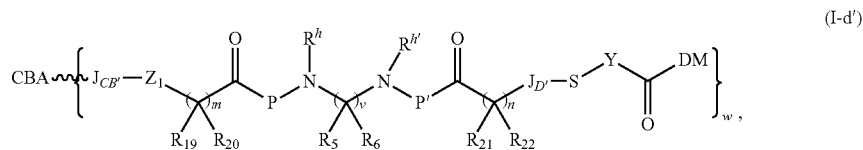
(I-d')

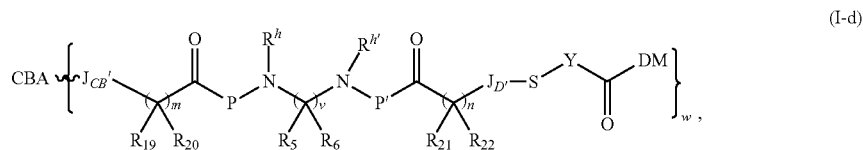
(I-d)

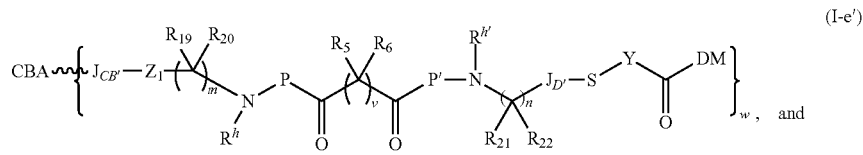
(I-e')

and

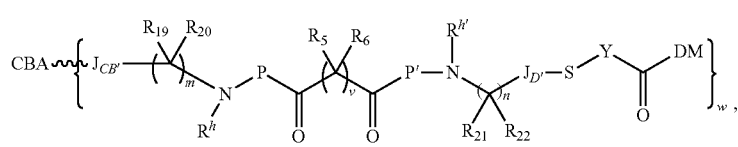

(I-e)

or a pharmaceutically acceptable salt thereof, in which the variables are as defined in the first embodiment or each of its alternative embodiments or its first or sixth specific embodiment. Preferably, P and P' are the same. In one embodiment, v is 0.

In a ninth specific embodiment, in Formula (I-a'), (I-a), (I-b'), (I-b), (I-c'), (I-c), (I-d'), (I-d), (I-e') or (I-e), $R_{19}$, $R_{20}$, $R_{21}$ and $R_{22}$ are each H, and the remainder of the variables are as defined in the first embodiment or each of its alternative embodiments or its first, second, third, fourth, fifth, sixth, seventh, or eighth specific embodiment.

In a tenth specific embodiment, in Formula (I-c'), (I-c), (I-d'), (I-d), (I-e') or (I-e), $R_5$ and $R_6$ are each H; and the remainder of the variables are as defined in the first embodiment or each of its alternative embodiments or the first, sixth, eighth, or ninth specific embodiment. Preferably, $R_5$ and $R_6$ are both H; and v is 2 or 3.

In an eleventh specific embodiment, in Formula (I'), (I), (I-a'), (I-a), (I-b'), (I-b), (I-c'), (I-c), (I-d'), (I-d), (I-e') or (I-e), the remainder of the variables are as defined in the first embodiment or each of its alternative embodiments or its first, second, third, fourth, fifth, sixth, seventh, eighth, ninth, or tenth specific embodiment.

In a fourteenth specific embodiment, in Formula (I'), (I), (I-a'), (I-a), (I-b'), (I-b), (I-c'), (I-c), (I-d'), (I-d), (I-e') or (I-e), P and P', for each occurrence, are independently $[XX]_3$; and the remainder of the variables are as defined in the first embodiment or each of its alternative embodiments or its first, second, third, fourth, fifth, sixth, seventh, eighth, ninth, or tenth specific embodiment.

In a fifteenth specific embodiment, the conjugate is represented by the following formula, or a pharmaceutically acceptable salt thereof:

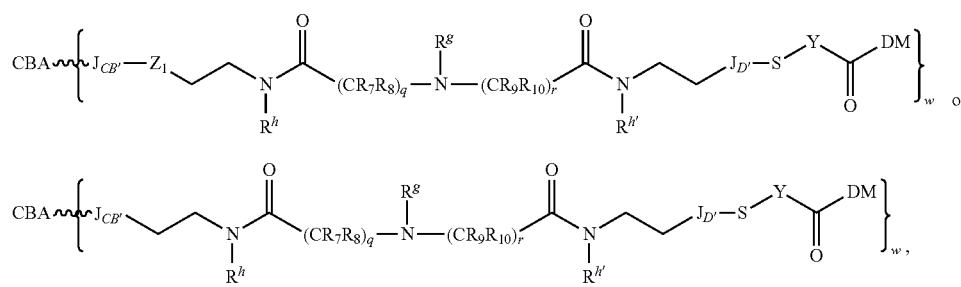

P and P', for each occurrence, are independently $[XX]_{1-10}$; and the remainder of the variables are as defined in the first embodiment or each of its alternative embodiments or its first, second, third, fourth, fifth, sixth, seventh, eighth, ninth, or tenth specific embodiment.

In a twelfth specific embodiment, in Formula (I'), (I), (I-a'), (I-a), (I-b'), (I-b), (I-c'), (I-c), (I-d'), (I-d), (I-e') or (I-e), P and P', for each occurrence, are independently $[XX]_{2-4}$; and the remainder of the variables are as defined in the first embodiment or each of its alternative embodiments or its first, second, third, fourth, fifth, sixth, seventh, eighth, ninth, or tenth specific embodiment.

In a thirteenth specific embodiment, in Formula (I'), (I), (I-a'), (I-a), (I-b'), (I-b), (I-c'), (I-c), (I-d'), (I-d), (I-e') or (I-e), P and P', for each occurrence, are independently $[XX]_2$; and in which the variables are as defined in the first embodiment or each of its alternative embodiments or its first, second, third, fourth, sixth, seventh, ninth, tenth, eleventh, twelfth, thirteenth, or fourteenth specific embodiment.

In a sixteenth specific embodiment, in Formula (I'), (I), (I-a'), (I-a), (I-c'), (I-c), (I-f') or (I-f), $R_7$ to $R_{10}$ are each H; and the remainder of the variables are as defined in the first embodiment or each of its alternative embodiments or its first, second, third, fourth, sixth, seventh, ninth, tenth, eleventh, twelfth, thirteenth, fourteenth, or fifteenth specific embodiment. Preferably, $R_7$ to $R_{10}$ are each H; and q and r are each 1.

In a seventeenth specific embodiment, the conjugate is represented by the following formula, or a pharmaceutically acceptable salt thereof:

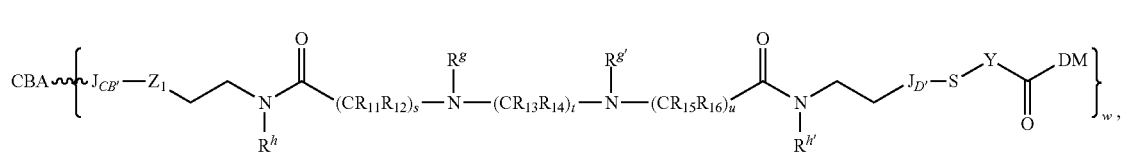

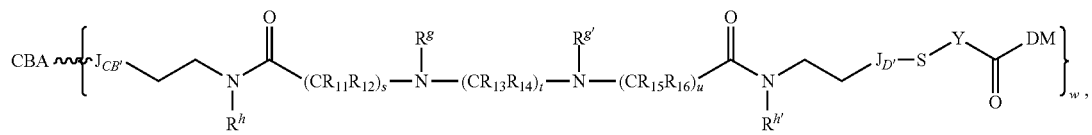

in which the variables are as defined in the first embodiment or each of its alternative embodiments or its first, second, third, fourth, sixth, seventh, ninth, tenth, eleventh, twelfth, thirteenth, or fourteenth specific embodiment.

In an eighteenth specific embodiment, in Formula (I'), (I), (I-a'), (I-a), (I-c'), (I-c), (I-g') or (I-g), $R_{11}$ to $R_{16}$ are each H; and the remainder of the variables are as defined in the first embodiment or each of its alternative embodiments or its first, second, third, fourth, sixth, seventh, ninth, tenth, eleventh, twelfth, thirteenth, fourteenth, or seventeenth specific embodiment. Preferably, $R_{11}$ to $R_{16}$ are each H; s and u are each 1 and t is 2.

In a nineteenth specific embodiment, in Formula (I'), (I), (I-a'), (I-a), (I-b'), (I-b), (I-c'), (I-c), (I-d'), (I-d), (I-e'), (I-e), (I-f'), (I-f), (I-g'), (I-g), (III') or (III), $J_{CB'}$ is

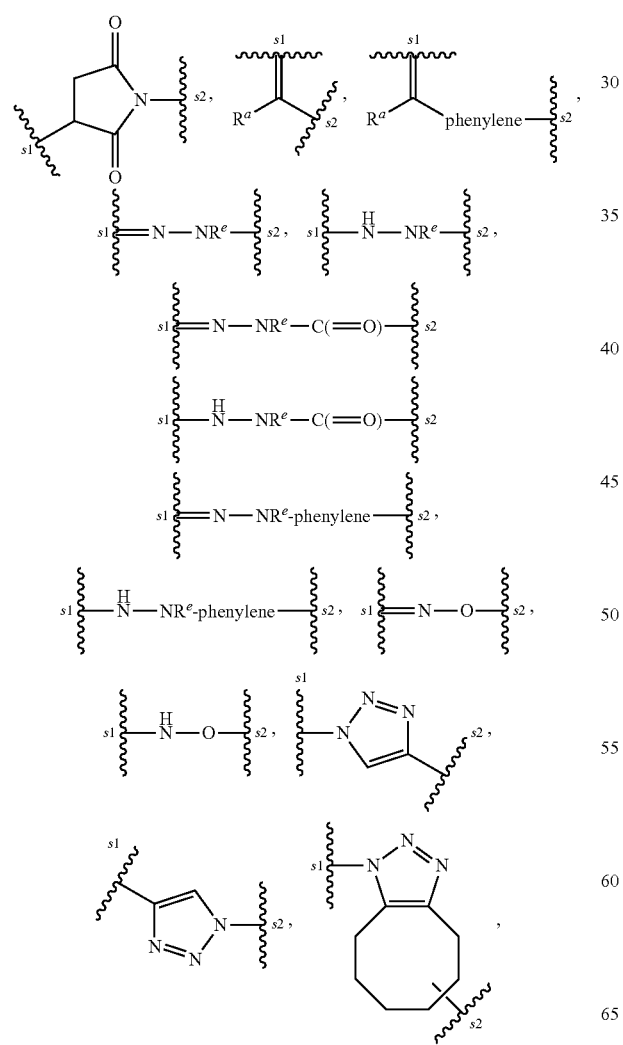

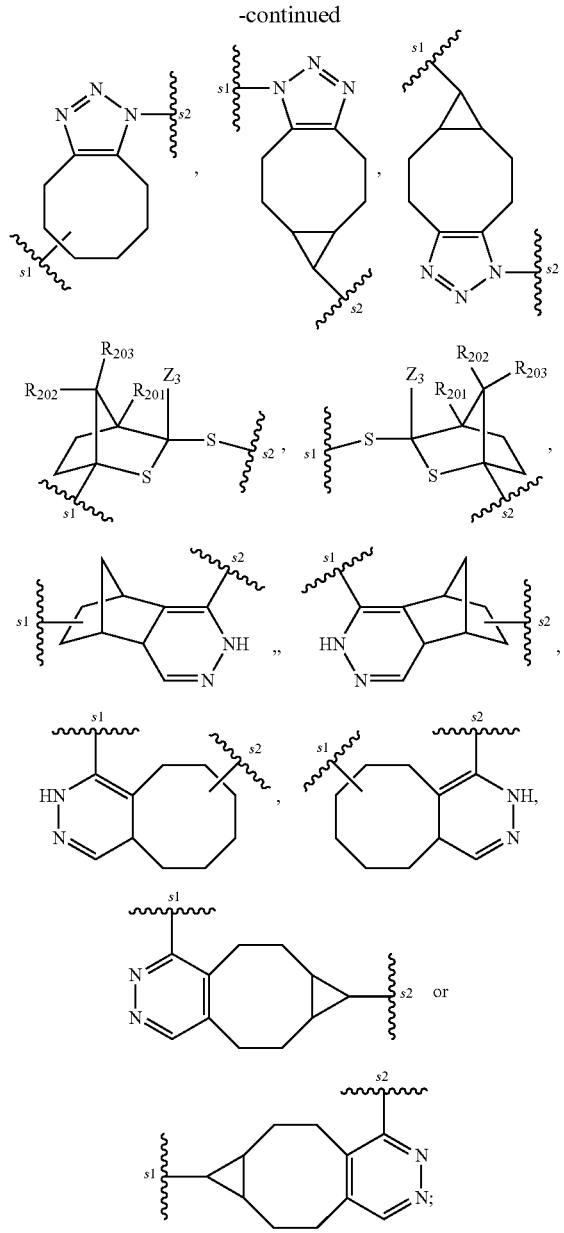

and the remainder of the variables are as defined in the first or second embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, or eighteenth specific embodiment.

In a twentieth specific embodiment, in Formula (I'), (I), (I-a'), (I-a), (I-b'), (I-b), (I-c'), (I-c), (I-d'), (I-d), (I-e'), (I-e), (I-f'), (I-f), (I-g'), (I-g), (III') or (III), $J_{D'}$ is

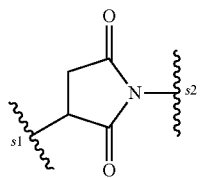 [SMILES: *C1CC(=O)N(*)C1=O]

and the remainder of the variables are as defined in the first or second embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, or nineteenth specific embodiment.

In a twenty-first specific embodiment, in Formula (I'), (I), (I-a'), (I-a), (I-b'), (I-b), (I-c'), (I-c), (I-d'), (I-d), (I-e'), (I-e), (I-f'), (I-f), (I-g'), (I-g), (III') or (III), $R^a$, $R^b$, $R^c$, and $R^e$ are each H; and the remainder of the variables are as defined in the first or second embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth specific embodiment.

In a twenty-second specific embodiment, the conjugate is represented by a formula selected from:

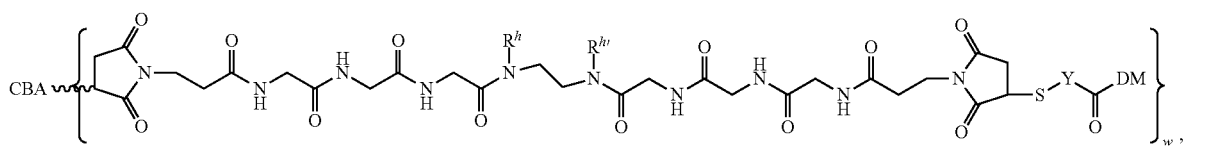

(I-h)

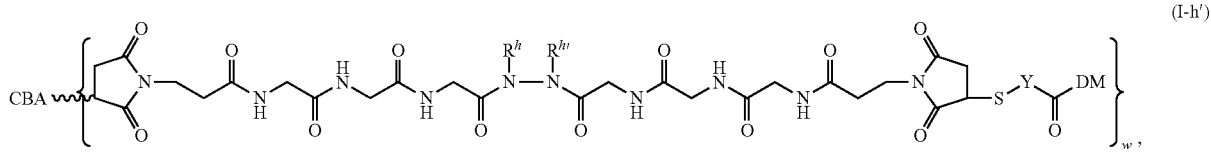

(I-h')

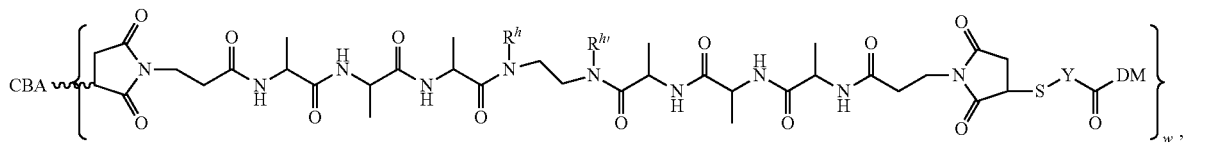

(I-i)

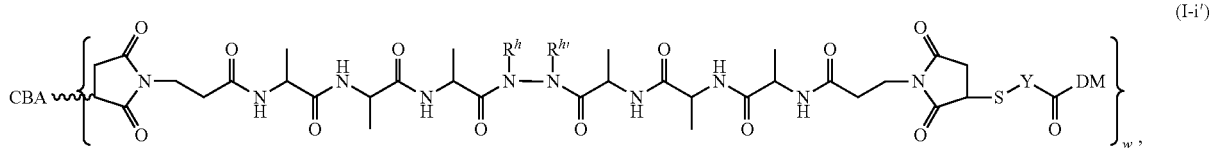

(I-i')

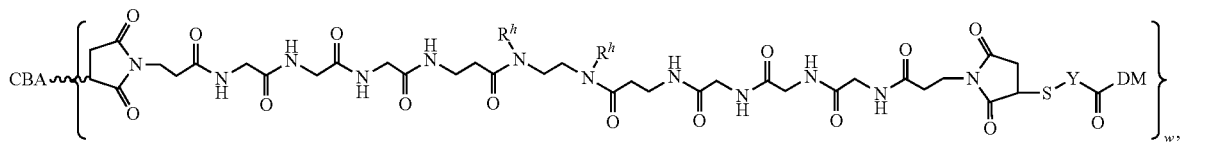

(I-j)

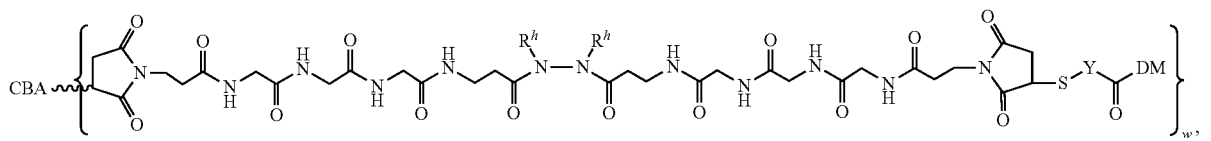

(I-j')

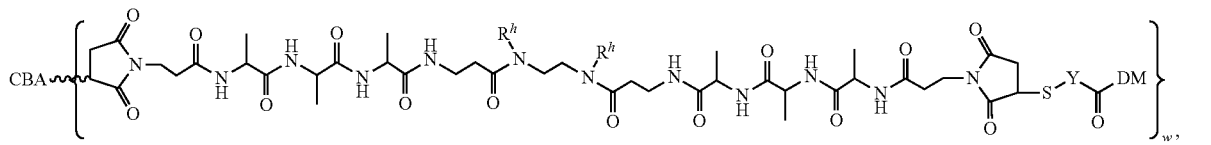

(I-k)

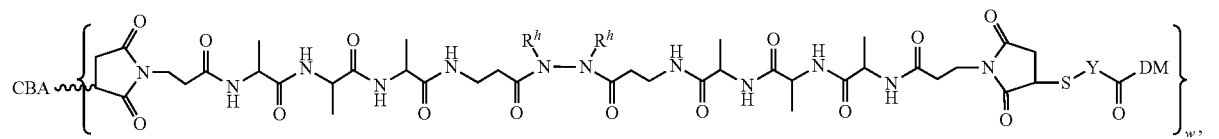
(I-k')
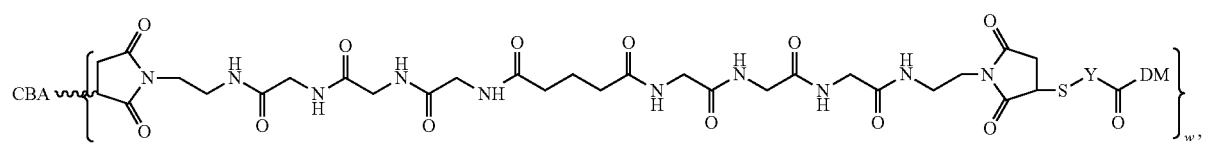
(I-l)
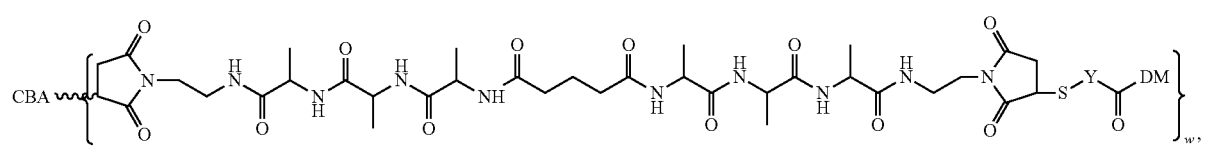
(I-m)
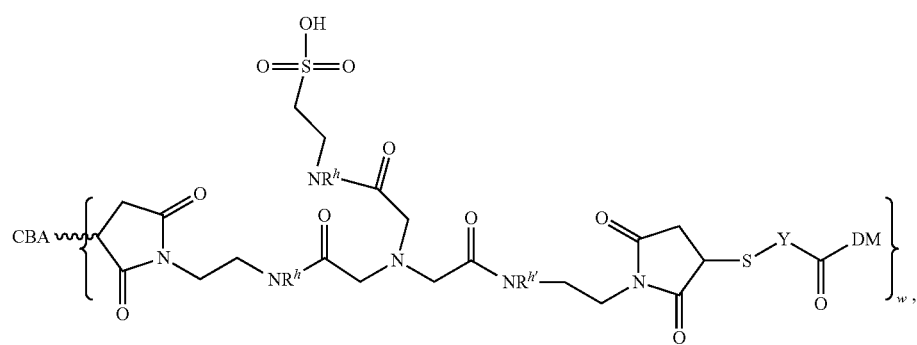
(I-n)
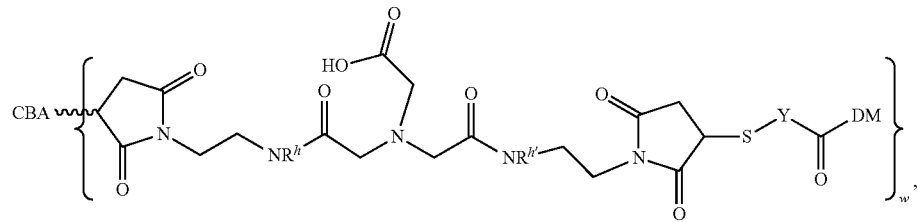
(I-o)
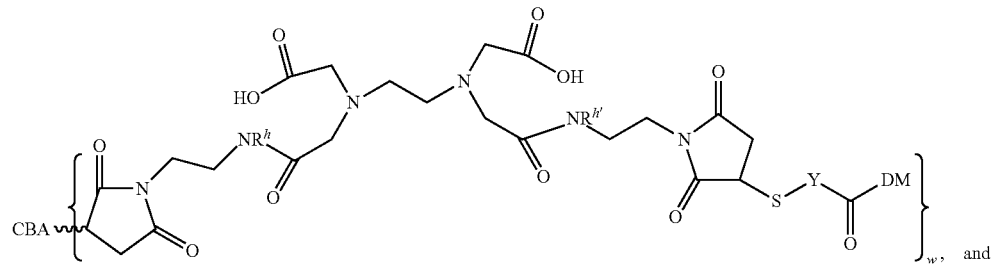
(I-p)
and

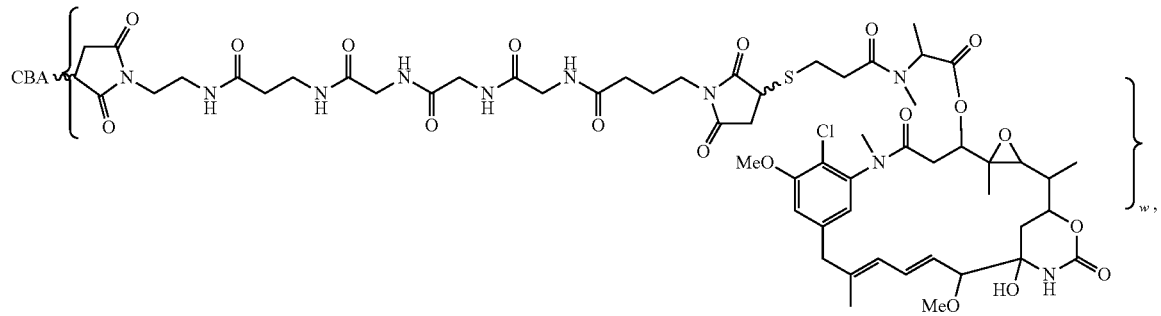

(I-q)

or a salt (e.g., pharmaceutically acceptable salt) thereof, in which the variables are as defined in the first embodiment.

In a twenty-third specific embodiment, Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-n), (I-o), or (I-p), $R^h$ and $R^{h'}$, for each occurrence, are independently H or methyl; and the remainder of the variables are as defined in the first embodiment or each of its alternative embodiments, or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second specific embodiment.

In a twenty-fourth specific embodiment, Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-n), (I-o), or (I-p), $R^h$ and $R^{h'}$ are each H; and the remainder of the variables are as defined in the first embodiment or each of its alternative embodiments, or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty third specific embodiment.

In a twenty-fifth specific embodiment, Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-n), (I-o), (I-p), (III') or (III), $R_1$ and $R_2$ are each independently H or an optionally substituted alkyl; $R_3$ and $R_4$ are each H; and i is an integer between 0 and 10; and the remainder of the variables are as defined in the first or second embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth specific embodiment. Preferably, $R_1$, $R_2$, $R_3$ and $R_4$ are all H. More preferably, $R_1$, $R_2$, $R_3$ and $R_4$ are all H; and i is 1.

In a twenty-sixth specific embodiment, in Formula (I'), (I), (I-a'), (I-a), (I-b'), (I-b), (I-c'), (I-c), (I-d'), (I-d), (I-e') or (I-e), m and n, for each occurrence, are independently an integer between 2 and 5; and the remainder of the variables are as defined in the first embodiment or each of its alternative embodiments or its first, second, third, fourth, fifth, sixth, seventh, eighth, ninth, tenth, eleventh, twelfth, thirteenth, fourteenth, sixteenth, eighteenth, nineteenth, twentieth, twenty-first, twenty-third, twenty-fourth, or twenty-fifth specific embodiment.

In a twenty-seven specific embodiment, in Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-l), (I-m), (I-n), (I-o), (I-p), (III') or (III), DM is a drug moiety represented by the following formula:

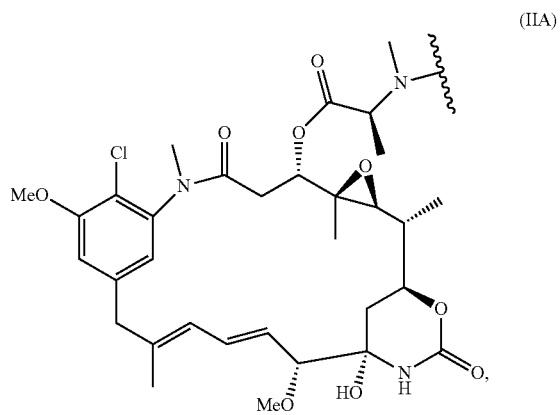 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

(IIA)

and the remainder of the variables are as defined in the first or second embodiment or each of their alternative embodiments, or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth specific embodiment.

In a twenty-eight specific embodiment, in Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-l), (I-m), (I-n), (I-o), (I-p), (III') or (III), Y is —$CH_2$—$CH_2$—; and the remainder of the variables are as defined in the first or second embodiment or each of their alternative embodiments, or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seven specific embodiment.

In Formula (I'), (I), (I-a'), (I-a), (I-b'), (I-b), (I-c'), (I-c), (I-d'), (I-d), (I-e'), (I-e), (I-f'), (I-f), (I-g'), (I-g), (I-h'), (I-h), (I-i'), (I-i), (I-j'), (I-j), (I-k'), (I-k), (I-l), (I-m), (I-n), (I-o), (I-p), (III') or (III), w is preferably an integer between 1 and 10, between 1 and 6, or alternatively, between 1 and 4; and the remainder of the variables are as defined in the first or second embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh specific embodiment.

Cytotoxic Compounds

The present invention also provides a cytotoxic compound represented by Formula (IV'), (IV), (V'), (V), (X') or (X) as described in the third or fourth embodiment and their alternative embodiments above. In addition, twenty-eight specific embodiments for the conjugate are further described below in this cytotoxic compound section.

In a first specific embodiment, the cytotoxic compound is represented by the following formula, or a salt (e.g., a pharmaceutically acceptable salt) thereof:

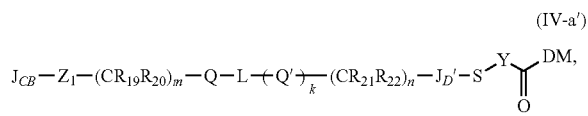

(IV-a')

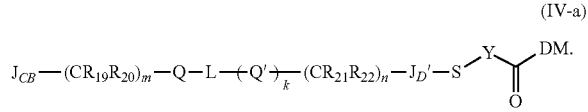

(IV-a)

In Formula (IV-a') or (IV-a) above, $R_{19}$ to $R_{22}$, for each occurrence, are independently H or an optionally substituted alkyl; m and n are each independently 0 to 10; and the remainder of the variables are as defined in the third embodiment or each of its alternative embodiments. Preferably, $R_{19}$ to $R_{22}$ are all H. Alternatively, $R_{19}$ to $R_{22}$ are all H; and m and n are 2.

In a second specific embodiment, in Formula (IV'), (IV), (IV-a') or (IV-a), the ionizable group is —$SO_3H$, —$Z'$—$SO_3H$, —$OPO_3H_2$, —$Z'$—$OPO_3H_2$, —$PO_3H_2$, —$Z'$—$PO_3H_2$, —$CO_2H$, —$Z'$—$CO_2H$, —$NR_{11}R_{12}$, or —$Z'$—$NR_{11}R_{12}$, and the charged group is —$N^+R_{23}R_{24}R_{25}X^-$, or —$Z'$—$N^+R_{23}R_{24}R_{25}X^-$; $Z'$ is an optionally substituted alkylene, an optionally substituted cycloalkylene or an optionally substituted phenylene; $R_{23}$ to $R_{25}$ are each independently an optionally substituted alkyl; and $X^-$ is an anion (e.g., a pharmaceutically acceptable anion). In this second specific embodiment, the remainder of the variables are as defined in the third embodiment or each of its alternative embodiments or its first specific embodiment.

In a third specific embodiment, within the ionizable group or the charged substituent described in the preceding paragraph immediately above, variable $Z'$ is alkylene and the remainder of the variables are as defined in the third embodiment or each of its alternative embodiments or its first or second specific embodiment.

In a fourth specific embodiment, in Formula (IV'), (IV), (IV-a') or (IV-a), V is H or —$CH_2CH_2SO_3H$ or a salt (e.g., a pharmaceutically acceptable salt) thereof; and the remainder of the variables are as defined in the third embodiment or each of its alternative embodiments or its first specific embodiment.

In a fifth specific embodiment, the cytotoxic compound is represented by the following formula, or a salt (e.g., a pharmaceutically acceptable salt) thereof:

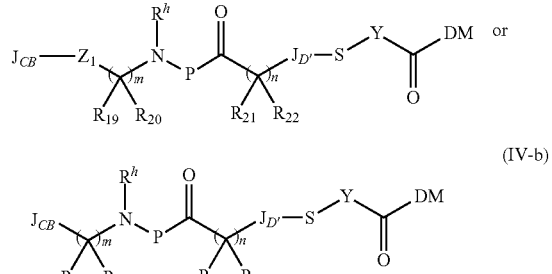

in which the variables are as defined in the third embodiment or each of its alternative embodiments or its first specific embodiment.

In a sixth specific embodiment, the cytotoxic compound is represented by the following formula, or a salt (e.g., a pharmaceutically acceptable salt) thereof:

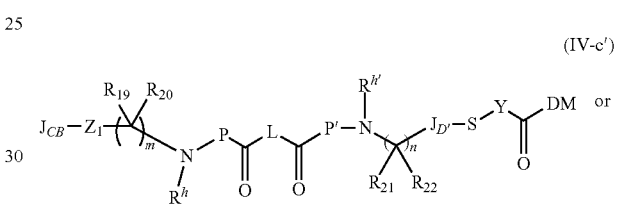

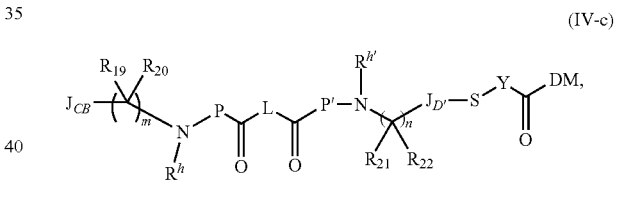

in which the variables are as defined in the third embodiment or each of its alternative embodiments or its first, second, third, or fourth specific embodiment. Preferably, P and P' are the same.

In a seventh specific embodiment, in Formula (IV'), (IV), (IV-a'), (IV-a), (IV-c') or (IV-c), L is —$(CR_7R_8)_q$—$N(R^8)$—$(CR_9R_{10})_r$— or —$(CR_{11}R_{12})_s$—$N(R^8)$—$(CR_{13}R_{14})_t$—$N(R^{g'})$—$(CR_{15}R_{16})_u$—; and the remainder of the variables are as defined in the third embodiment or each of its alternative embodiments or its first, second, third, fourth, or sixth specific embodiment.

In an eighth specific embodiment, the cytotoxic compound is represented by a formula selected from:

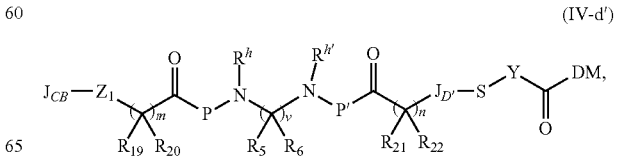

-continued

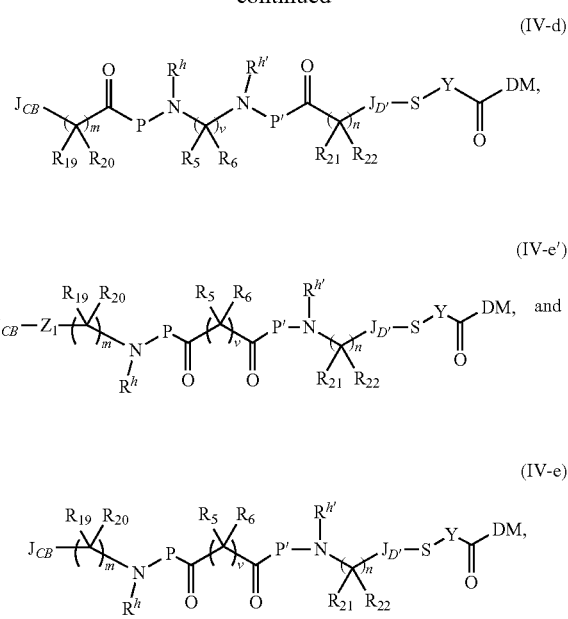

or a salt (e.g., a pharmaceutically acceptable salt) thereof, in which the variables are as defined in the third embodiment or each of its alternative embodiments, or its first or sixth specific embodiment. Preferably, P and P' are the same. In one embodiment, v is 0.

In a ninth specific embodiment, in Formula (IV-a'), (IV-a), (IV-b'), (IV-b), (IV-c'), (IV-c), (IV-d'), (IV-d), (IV-e') or (IV-e), $R_{19}$, $R_{20}$, $R_{21}$ and $R_{22}$ are each H, and the remainder of the variables are as defined in the third embodiment or each of its alternative embodiments, or its first, second, third, fourth, fifth, sixth, seventh, or eighth specific embodiment.

In a tenth specific embodiment, in Formula (IV'), (IV), (IV-a'), (IV-a), (IV-c'), (IV-c), (IV-d'), (IV-d), (IV-e') or (IV-e), $R_5$ and $R_6$ are each H; and the remainder of the variables are as defined in the third embodiment or each of its alternative embodiments, or the first, sixth, eighth, or ninth specific embodiment. Preferably, $R_5$ and $R_6$ are both H; and v is 2 or 3.

In an eleventh specific embodiment, in Formula (IV'), (IV), (IV-a'), (IV-a), (IV-b'), (IV-b), (IV-c'), (IV-c), (IV-d'), (IV-d), (IV-e') or (IV-e), P and P', for each occurrence, are independently $[XX]_{1-10}$; and the remainder of the variables are as defined in the third embodiment or each of its alternative embodiments, or its first, second, third, fourth, fifth, sixth, seventh, eighth, ninth, or tenth specific embodiment.

In a twelfth specific embodiment, in Formula (IV'), (IV), (IV-a'), (IV-a), (IV-b'), (IV-b), (IV-c'), (IV-c), (IV-d'), (IV-d), (IV-e') or (IV-e), P and P', for each occurrence, are independently $[XX]_{2-4}$; and the remainder of the variables are as defined in the third embodiment or each of its alternative embodiments, or its first, second, third, fourth, fifth, sixth, seventh, eighth, ninth, or tenth specific embodiment.

In a thirteenth specific embodiment, in Formula (IV'), (IV), (IV-a'), (IV-a), (IV-b'), (IV-b), (IV-c'), (IV-c), (IV-d'), (IV-d), (IV-e') or (IV-e), P and P', for each occurrence, are independently $[XX]_2$; and the remainder of the variables are as defined in the third embodiment or each of its alternative embodiments, or its first, second, third, fourth, fifth, sixth, seventh, eighth, ninth, or tenth specific embodiment.

In a fourteenth specific embodiment, in Formula (IV'), (IV), (IV-a'), (IV-a), (IV-b'), (IV-b), (IV-c'), (IV-c), (IV-d'), (IV-d), (IV-e') or (IV-e), P and P', for each occurrence, are independently $[XX]_3$; and the remainder of the variables are as defined in the third embodiment or each of its alternative embodiments, or its first, second, third, fourth, fifth, sixth, seventh, eighth, ninth, or tenth specific embodiment.

In a fifteenth specific embodiment, the cytotoxic compound is represented by the following formula, or a salt (e.g., a pharmaceutically acceptable salt) thereof:

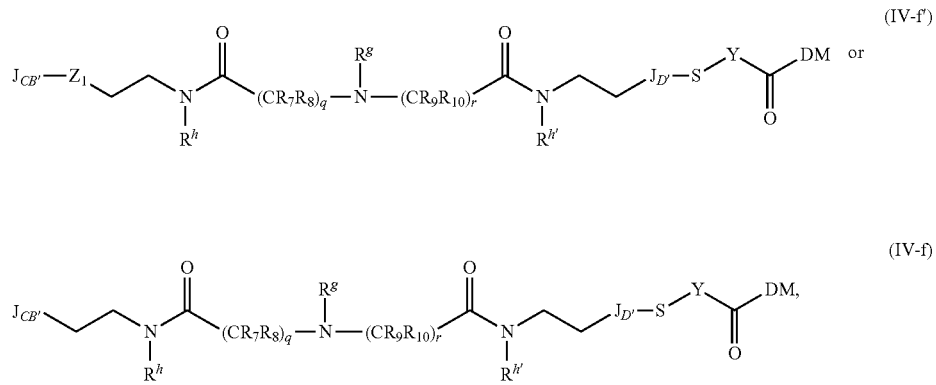

in which the variables are as defined in the third embodiment or each of its alternative embodiments, or its first, second, third, fourth, sixth, seventh, ninth, tenth, eleventh, twelfth, thirteenth, or fourteenth specific embodiment.

In a sixteenth specific embodiment, in Formula (IV'), (IV), (IV-a'), (IV-a), (IV-c'), (IV-c), (IV-f') or (IV-f), $R_7$ to $R_{10}$ are each H; and the remainder of the variables are as defined in the third embodiment or each of its alternative embodiments, or its first, second, third, fourth, sixth, seventh, ninth, tenth, eleventh, twelfth, thirteenth, fourteenth, or fifteenth specific embodiment. Preferably, $R_7$ to $R_{10}$ are each H; and q and r are each 1.

In a seventeenth specific embodiment, the cytotoxic compound is represented by the following formula, or a salt (e.g., a pharmaceutically acceptable salt) thereof:

$$J_{CB}-Z_1-\text{...}-N(R^h)-C(=O)-(CR_{11}R_{12})_s-N(R^g)-(CR_{13}R_{14})_t-N(R^{g'})-(CR_{15}R_{16})_u-C(=O)-N(R^{h'})-\text{...}-J_{D'}-S-Y-C(=O)-DM, \quad \text{or} \quad (IV\text{-}g')$$

$$J_{CB}-\text{...}-N(R^h)-C(=O)-(CR_{11}R_{12})_s-N(R^g)-(CR_{13}R_{14})_t-N(R^{g'})-(CR_{15}R_{16})_u-C(=O)-N(R^{h'})-\text{...}-J_{D'}-S-Y-C(=O)-DM, \quad (IV\text{-}g)$$

in which the variables are as defined in the third embodiment or each of its alternative embodiments, or its first, second, third, fourth, sixth, seventh, ninth, tenth, eleventh, twelfth, thirteenth, or fourteenth specific embodiment.

In an eighteenth specific embodiment, in Formula (IV'), (IV), (IV-a'), (IV-a), (IV-c'), (IV-c), (IV-g') or (IV-g), $R_{11}$ to $R_{16}$ are each H; and the remainder of the variables are as defined in the third embodiment or each of its alternative embodiments, or its first, second, third, fourth, sixth, seventh, ninth, tenth, eleventh, twelfth, thirteenth, fourteenth, or seventeenth specific embodiment. Preferably, $R_{11}$ to $R_{16}$ are each H; s and u are each 1 and t is 2.

In a nineteenth specific embodiment, in Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (V') or (V), $J_{CB}$ is maleimide, (maleimide structure)

$R^a$—C(=O)—, $R^a$—C(=O)-phenylene-, $NH_2$—$NR^e$—C(=O)—, $NH_2$—$NR^e$-phenylene-, $NH_2$—O—, —$N_3$, —C≡CH, (cyclooctyne), (bicyclononyne), (cyclopentadiene with $R_{201}$, $R_{202}$, $R_{203}$), (dithioester with $Z_2$), (tetrazine), (norbornene) or (trans-cyclooctene);

and the remainder of the variables are as defined in the third or fourth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, or eighteenth specific embodiment.

In a twentieth specific embodiment, in Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (V') or (V), $J_{D'}$ is (succinimide with s1, s2 substituents)

and the remainder of the variables are as defined in the third or fourth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, or nineteenth specific embodiment.

In a twenty-first specific embodiment, in Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (V') or (V), $R^a$, $R^b$, $R^e$, and $R^e$ are each H; and the remainder of the variables are as defined in the third or fourth embodiment or each of their alternative embodiments, or their first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth specific embodiment.

In a twenty-second specific embodiment, the cytotoxic compound is represented by a formula selected from:

(IV-h)

(maleimide-linker-DM structure with multiple glycine/amide units, $R^h$, $R^{h'}$ substituents, and succinimide-S-Y-C(=O)-DM terminus)

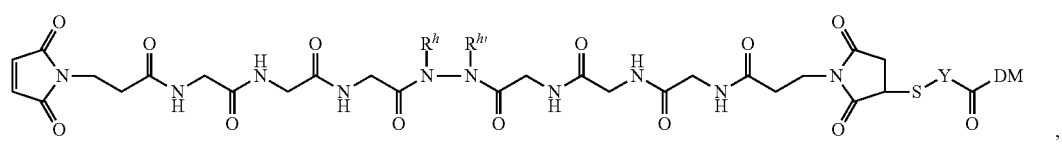
(IV-h′)
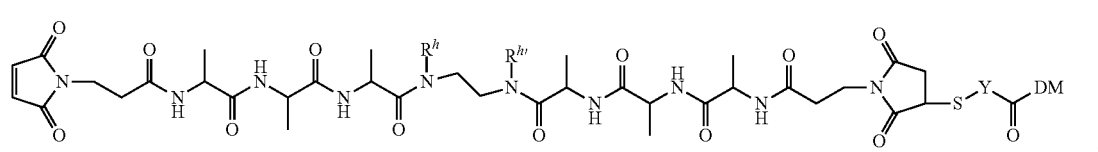
(IV-i)
(IV-i′)
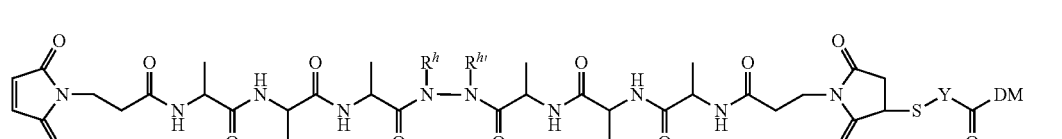
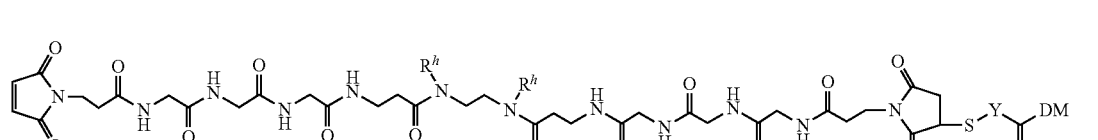
(IV-j)
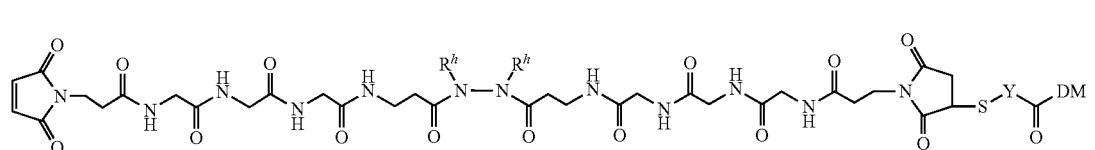
(IV-j′)
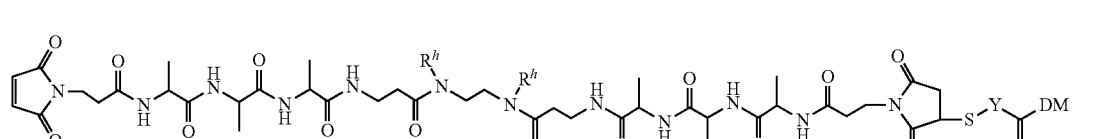
(IV-k)
(IV-k′)
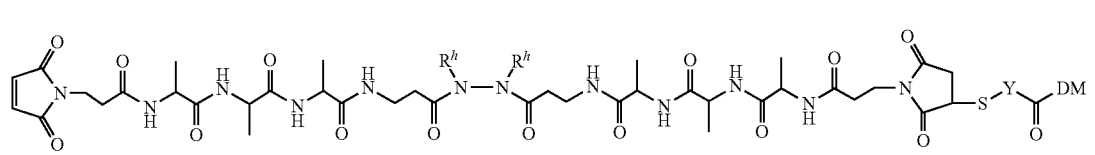
(IV-l)
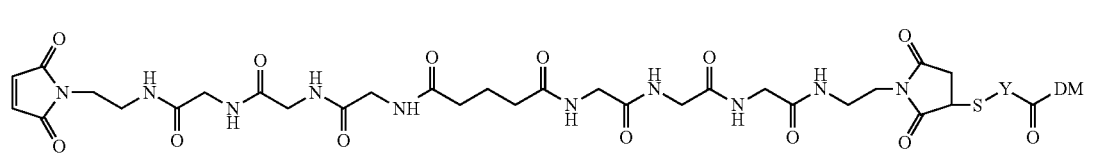
(IV-m)
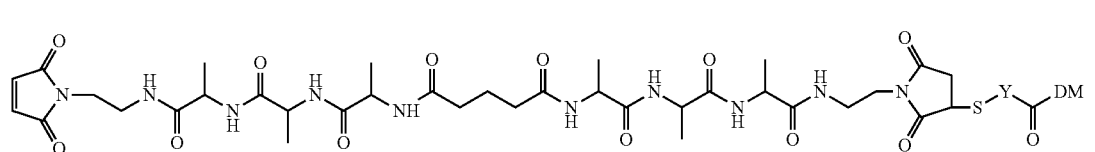

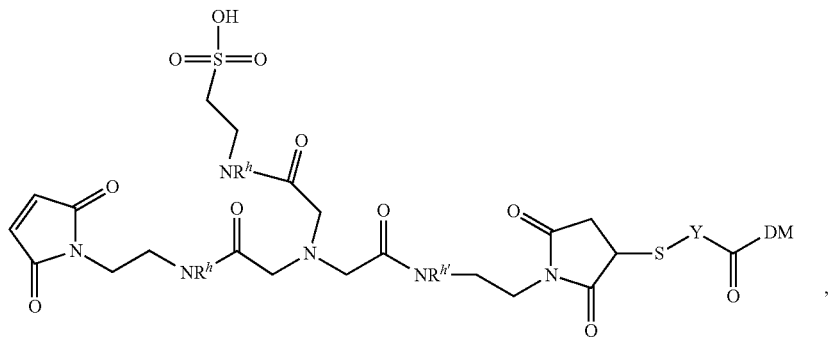
(IV-n)

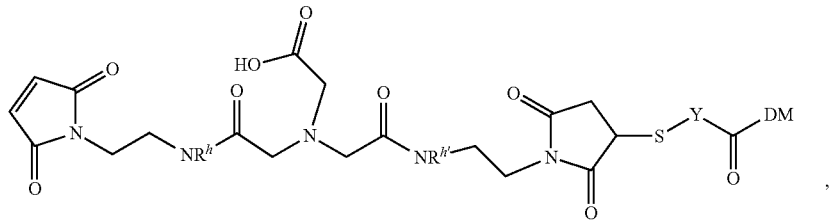
(IV-o)

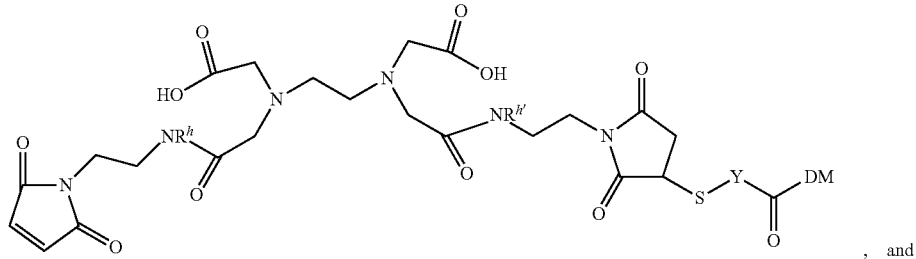
, and
(IV-p)

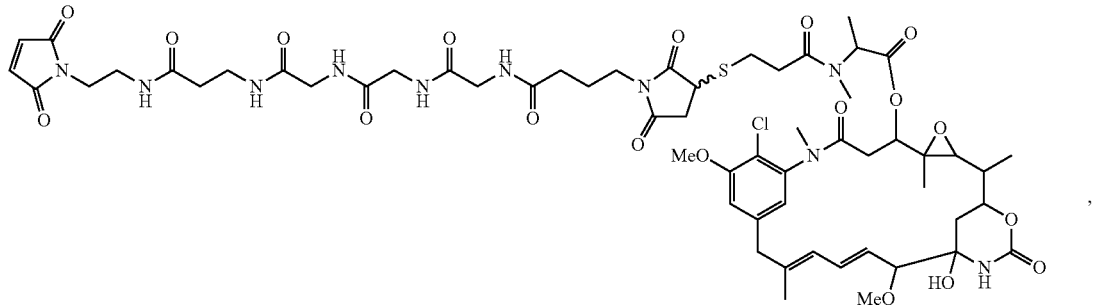
(IV-q)

or a salt (e.g., a pharmaceutically acceptable salt) thereof, in which the variables are as defined in the third embodiment.

In a twenty-third specific embodiment, Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (IV-h'), (IV-h), (IV-i'), (IV-i), (IV-j'), (IV-j), (IV-k'), (IV-k), (IV-n), (IV-o), or (IV-p), $R^h$ and $R^{h'}$, for each occurrence, are independently H or methyl; and the remainder of the variables are as defined in the third embodiment or each of its alternative embodiments, or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second specific embodiment.

In a twenty-fourth specific embodiment, Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (IV-h'), (IV-h), (IV-i'), (IV-i), (IV-j'), (IV-j), (IV-k'), (IV-k), (IV-n), (IV-o), or (IV-p), $R^h$ and $R^{h'}$ are each H; and the remainder of the variables are as defined in the third embodiment or each of its alternative embodiments, or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third specific embodiment.

In a twenty-fifth specific embodiment, Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (IV-h'), (IV-h), (IV-i'), (IV-i), (IV-j'), (IV-j), (IV-k'), (IV-k), (IV-n), (IV-o), (IV-p), (V') or (V), $R_1$ and $R_2$ are each independently H or an optionally substituted alkyl; $R_3$ and $R_4$ are each H; and i is an integer between 0 and 10; and the remainder of the variables are as defined in the third or fourth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth specific embodiment. Preferably, $R_1$, $R_2$, $R_3$ and $R_4$ are all H. More preferably, $R_1$, $R_2$, $R_3$ and $R_4$ are all H; and i is 1.

In a twenty-sixth specific embodiment, in Formula (IV'), (IV), (IV-a'), (IV-a), (IV-b'), (IV-b), (IV-c'), (IV-c), (IV-d'), (IV-d), (IV-e') or (IV-e), m and n, for each occurrence, are independently an integer between 2 and 5; and the remainder of the variables are as defined in the third embodiment or each of its alternative embodiments or its first, second, third, fourth, fifth, sixth, seventh, eighth, ninth, tenth, eleventh, twelfth, thirteenth, fourteenth, sixteenth, eighteenth, nineteenth, twentieth, twenty-first, twenty-third, twenty-fourth, or twenty-fifth specific embodiment.

In a twenty-seven specific embodiment, in Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (IV-h'), (IV-h), (IV-i'), (IV-i), (IV-j'), (IV-j), (IV-k'), (IV-k), (IV-l), (IV-m), (IV-n), (IV-o), (IV-p), (V') or (V), DM is a drug moiety represented by the following formula:

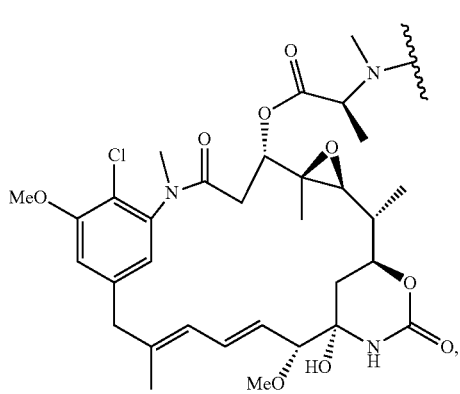

(IIA)

and the remainder of the variables are as defined in the third or fourth embodiment or each of their alternative embodiments, or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth specific embodiment.

In a twenty-eight specific embodiment, in Formula (IV'), (IV), (IV-a'), (IV-a), (IV-b'), (IV-b), (IV-c'), (IV-c), (IV-d'), (IV-d), (IV-e'), (IV-e), (IV-f'), (IV-f), (IV-g'), (IV-g), (IV-h'), (IV-h), (IV-i'), (IV-i), (IV-j'), (IV-j), (IV-k'), (IV-k), (IV-l), (IV-m), (IV-n), (IV-o), (IV-p), (V') or (V), Y is —CH$_2$—CH$_2$—; and the remainder of the variables are as defined in the third or fourth embodiment or each of their alternative embodiments, or their first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth or twenty-seven specific embodiment.

Linker Compounds

The present invention further provides a linker compound represented by Formula (VI'), (VI), (VII'), (VII), (XI') or (XI) as described in the fifth or sixth embodiment above. In addition, twenty-fifth specific embodiments for the conjugate are further described below in this linker compound section.

In a first specific embodiment, the linker compound is represented by the following formula, or a salt (e.g., a pharmaceutically acceptable salt) thereof:

(VI-a')

(VI-a)

In Formula (VI-a') or (VI-a) above, $R_{19}$ to $R_{22}$, for each occurrence, are independently H or an optionally substituted alkyl; m and n are each independently 0 to 10; and the remainder of the variables are as defined in the fifth embodiment or each of its alternative embodiments. Preferably, $R_{19}$ to $R_{22}$ are all H. Alternatively, $R_{19}$ to $R_{22}$ are all H; and m and n are 2.

In a second specific embodiment, in Formula (VI'), (VI), (VI-a') or (VI-a), the ionizable group is —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, and the charged group is —N$^+$R$_{23}$R$_{24}$R$_{25}$X$^-$, or —Z'—N$^+$R$_{23}$R$_{24}$R$_{25}$X$^-$; Z' is an optionally substituted alkylene, an optionally substituted cycloalkylene or an optionally substituted phenylene; $R_{23}$ to $R_{25}$ are each independently an optionally substituted alkyl; and X$^-$ is an anion (e.g., a pharmaceutically acceptable anion). In this second specific embodiment, the remainder of the variables are as defined in the fifth embodiment or each of its alternative embodiments or its first specific embodiment.

In a third specific embodiment, within the ionizable group or the charged substituent described in the preceding paragraph immediately above, variable Z' is alkylene and the remainder of the variables are as defined in the fifth embodiment or each of its alternative embodiments or its first or second specific embodiment.

In a fourth specific embodiment, in Formula (VI'), (VI), (VI-a') or (VI-a), V is H or —CH$_2$CH$_2$SO$_3$H or a salt (e.g., a pharmaceutically acceptable salt) thereof; and the remainder of the variables are as defined in the fifth embodiment or each of its alternative embodiments or its first specific embodiment.

In a fifth specific embodiment, the linker compound is represented by the following formula, or a salt (e.g., a pharmaceutically acceptable salt) thereof:

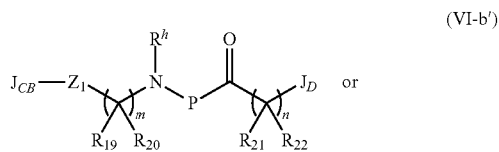

(VI-b')

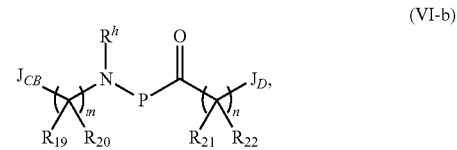

(VI-b)

in which the variables are as defined in the fifth embodiment or each of its alternative embodiments or its first specific embodiment.

In a sixth specific embodiment, the linker compound is represented by the following formula, or a salt (e.g., a pharmaceutically acceptable salt) thereof:

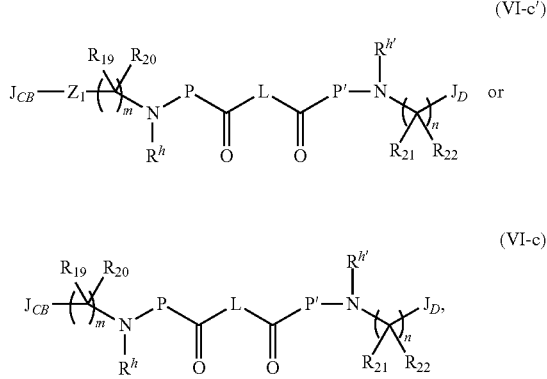

in which the variables are as defined in the fifth embodiment or each of its alternative embodiments or its first, second, third, or fourth specific embodiment. Preferably, P and P' are the same.

In a seventh specific embodiment, in Formula (VI'), (VI), (VI-a'), (VI-a), (VI-c') or (VI-c), L is —$(CR_7R_8)_q$—$N(R^g)$—$(CR_9R_{10})_r$— or —$(CR_{11}R_{12})_s$—$N(R^g)$—$(CR_{13}R_{14})_t$—$N(R^{g'})$—$(CR_{15}R_{16})_u$—; and the remainder of the variables are as defined in the fifth embodiment or each of its alternative embodiments or its first, second, third, fourth, or sixth specific embodiment.

In an eighth specific embodiment, the linker compound is represented by a formula selected from:

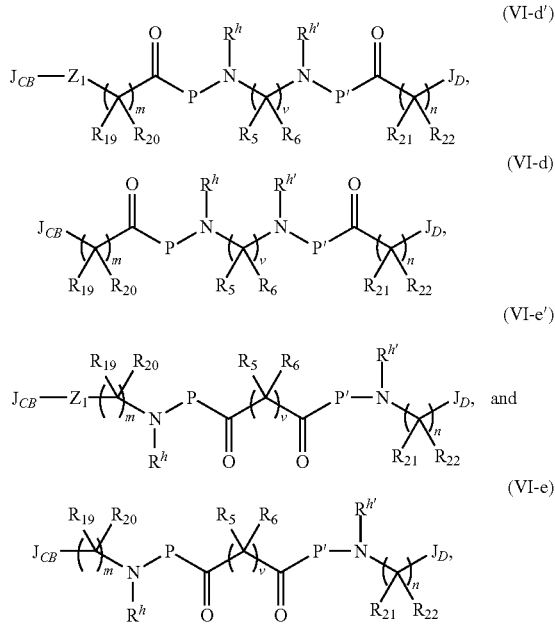

or a salt (e.g., a pharmaceutically acceptable salt) thereof, in which the variables are as defined in the fifth embodiment or each of its alternative embodiments, or its first or sixth specific embodiment. Preferably, P and P' are the same. In one embodiment, v is 0.

In a ninth specific embodiment, in Formula (VI-a'), (VI-a), (VI-b'), (VI-b), (VI-c'), (VI-c), (VI-d'), (VI-d), (VI-e') or (VI-e), $R_{19}$, $R_{20}$, $R_{21}$ and $R_{22}$ are each H, and the remainder of the variables are as defined in the fifth embodiment or each of its alternative embodiments, or its first, second, third, fourth, fifth, sixth, seventh, or eighth specific embodiment.

In a tenth specific embodiment, in Formula (VI'), (VI), (VI-a'), (VI-a), (VI-c'), (VI-c), (VI-d'), (VI-d), (VI-e') or (VI-e), $R_5$ and $R_6$ are each H; and the remainder of the variables are as defined in the fifth embodiment or each of its alternative embodiments, or the first, sixth, eighth, or ninth specific embodiment. Preferably, $R_5$ and $R_6$ are both H; and v is 2 or 3.

In an eleventh specific embodiment, in Formula (VI'), (VI), (VI-a'), (VI-a), (VI-b'), (VI-b), (VI-c'), (VI-c), (VI-d'), (VI-d), (VI-e') or (VI-e), P and P', for each occurrence, are independently $[XX]_{1-10}$; and the remainder of the variables are as defined in the fifth embodiment or each of its alternative embodiments, or its first, second, third, fourth, fifth, sixth, seventh, eighth, ninth, or tenth specific embodiment.

In a twelfth specific embodiment, in Formula (VI'), (VI), (VI-a'), (VI-a), (VI-b'), (VI-b), (VI-c'), (VI-c), (VI-d'), (VI-d), (VI-e'), or (VI-e), P and P', for each occurrence, are independently $[XX]_{2-4}$; and the remainder of the variables are as defined in the fifth embodiment or each of its alternative embodiments, or its first, second, third, fourth, fifth, sixth, seventh, eighth, ninth, or tenth specific embodiment.

In a thirteenth specific embodiment, in Formula (VI'), (VI), (VI-a'), (VI-a), (VI-b'), (VI-b), (VI-c'), (VI-c), (VI-d'), (VI-d), (VI-e') or (VI-e), P and P', for each occurrence, are independently $[XX]_2$; and the remainder of the variables are as defined in the fifth embodiment or each of its alternative embodiments, or its first, second, third, fourth, fifth, sixth, seventh, eighth, ninth, or tenth specific embodiment.

In a fourteenth specific embodiment, in Formula (VI'), (VI), (VI-a'), (VI-a), (VI-b'), (VI-b), (VI-c'), (VI-c), (VI-d'), (VI-d), (VI-e') or (VI-e), P and P', for each occurrence, are independently $[XX]_3$; and the remainder of the variables are as defined in the fifth embodiment or each of its alternative embodiments, or its first, second, third, fourth, fifth, sixth, seventh, eighth, ninth, or tenth specific embodiment.

In a fifteenth specific embodiment, the linker compound is represented by the following formula, or a salt (e.g., a pharmaceutically acceptable salt) thereof:

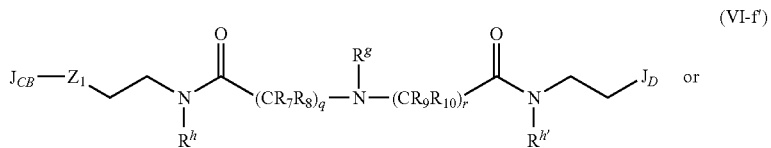

(VI-f)

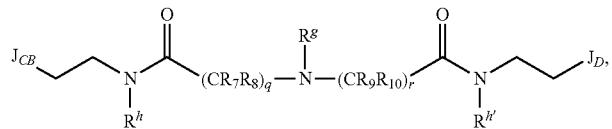

in which the variables are as defined in the fifth embodiment or each of its alternative embodiments or its first, second, third, fourth, sixth, seventh, ninth, tenth, eleventh, twelfth, thirteenth, or fourteenth specific embodiment.

In a sixteenth specific embodiment, in Formula (VI'), (VI), (VI-a'), (VI-a), (VI-c'), (VI-c), (VI-f') or (VI-f), $R_7$ to $R_{10}$ are each H; and the remainder of the variables are as defined in the fifth embodiment or each of its alternative embodiments or its first, second, third, fourth, sixth, seventh, ninth, tenth, eleventh, twelfth, thirteenth, fourteenth, or fifteenth specific embodiment. Preferably, $R_7$ to $R_{10}$ are each H; and q and r are each 1.

In a seventeenth specific embodiment, the linker compound is represented by the following formula, or a salt (e.g., a pharmaceutically acceptable salt) thereof:

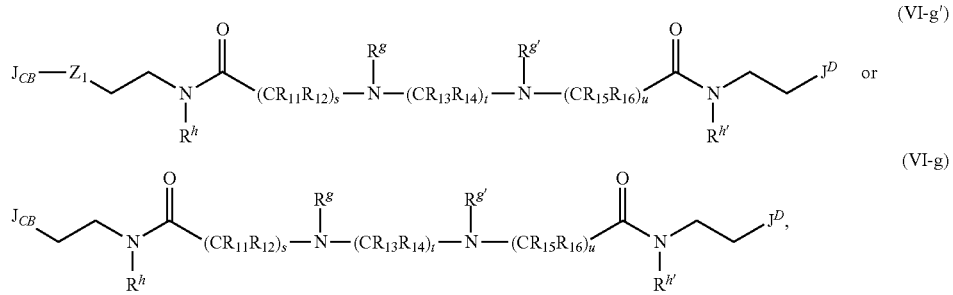

in which the variables are as defined in the fifth embodiment or each of its alternative embodiments or its first, second, third, fourth, sixth, seventh, ninth, tenth, eleventh, twelfth, thirteenth, or fourteenth specific embodiment.

In an eighteenth specific embodiment, in Formula (VI'), (VI), (VI-a'), (VI-a), (VI-c'), (VI-c), (VI-g') or (VI-g), $R_{11}$ to $R_{16}$ are each H; and the remainder of the variables are as defined in the fifth embodiment or each of its alternative embodiments or its first, second, third, fourth, sixth, seventh, ninth, tenth, eleventh, twelfth, thirteenth, fourteenth, or seventeenth specific embodiment. Preferably, $R_{11}$ to $R_{16}$ are each H; s and u are each 1 and t is 2.

In a nineteenth specific embodiment, in Formula (VI'), (VI), (VI-a'), (VI-a), (VI-b'), (VI-b), (VI-c'), (VI-c), (VI-d'), (VI-d), (VI-e'), (VI-e), (VI-f'), (VI-f), (VI-g'), (VI-g), (VII') or (VII), $J_{CB}$ is maleimide,

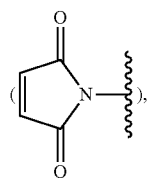

$R^a$—C(=O)—, $R^a$—C(=O)-phenylene-, $NH_2$—$NR^e$—C(=O)—, $NH_2$—$NR^e$-phenylene-, $NH_2$—O—, —$N_3$, —C≡CH,

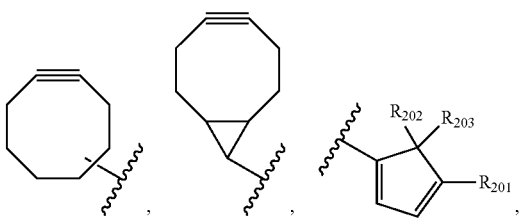

-continued

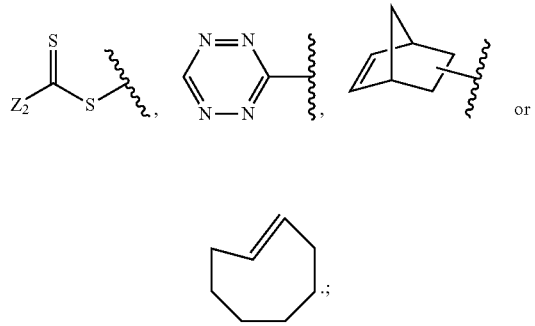

and the remainder of the variables are as defined in the fifth or sixth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, or eighteenth specific embodiment.

In a twentieth specific embodiment, in Formula (VI'), (VI), (VI-a'), (VI-a), (VI-b'), (VI-b), (VI-c'), (VI-c), (VI-d'), (VI-d), (VI-e'), (VI-e), (VI-f'), (VI-f), (VI-g'), (VI-g), (VII') or (VII), $J_D$ is

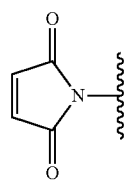 [SMILES: *N1C(=O)C=CC1=O]

and the remainder of the variables are as defined in the fifth or sixth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, or nineteenth specific embodiment.

In a twenty-first specific embodiment, in Formula (VI'), (VI), (VI-a'), (VI-a), (VI-b'), (VI-b), (VI-c'), (VI-c), (VI-d'), (VI-d), (VI-e'), (VI-e), (VI-f'), (VI-f), (VI-g'), (VI-g), (VII') or (VII), $R^a$, $R^b$, $R^c$, and $R^e$ are each H; and the remainder of the variables are as defined in the fifth or sixth embodiment or each of their alternative embodiments or their first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth specific embodiment.

In a twenty-second specific embodiment, the linker compound is represented by a formula selected from:

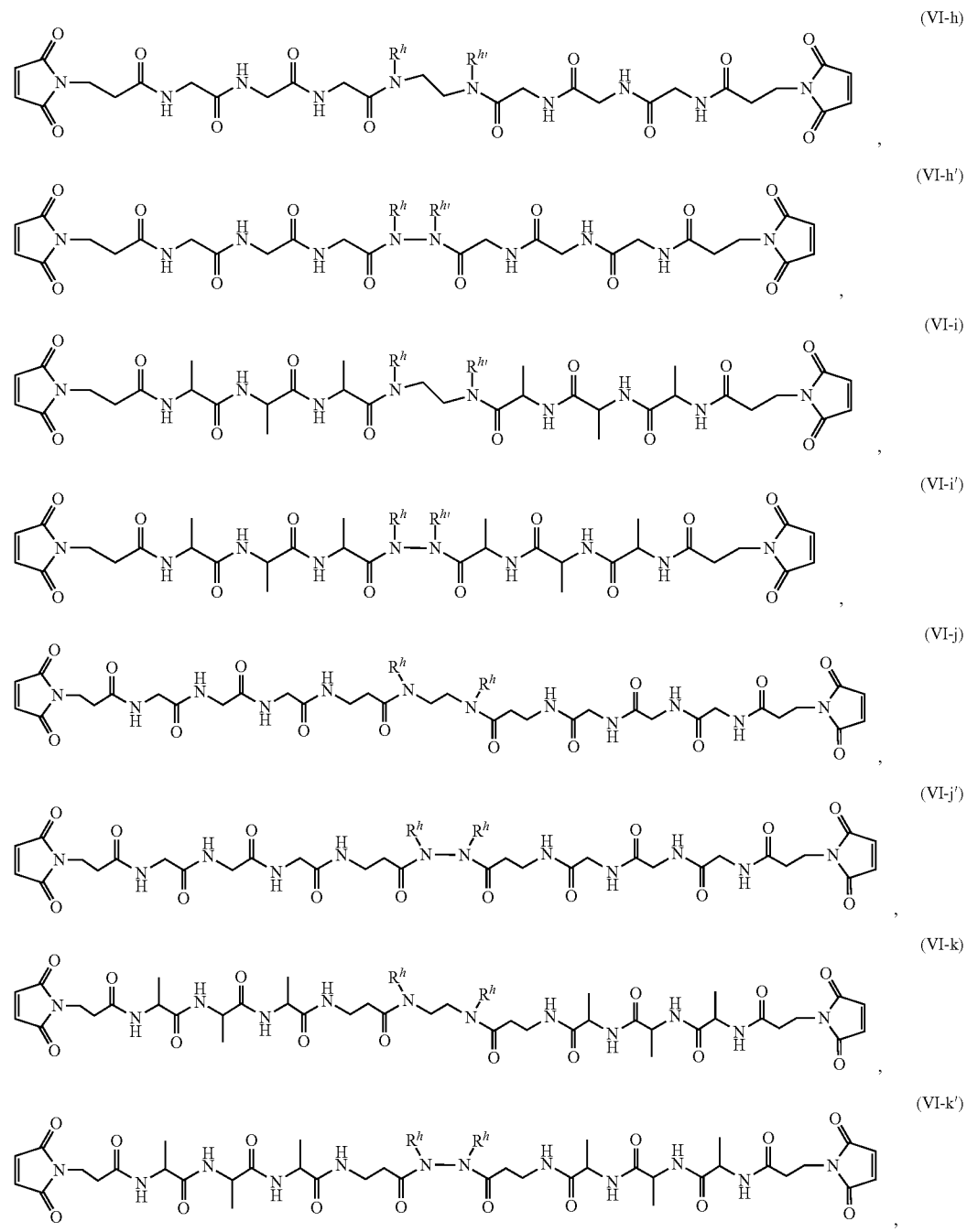

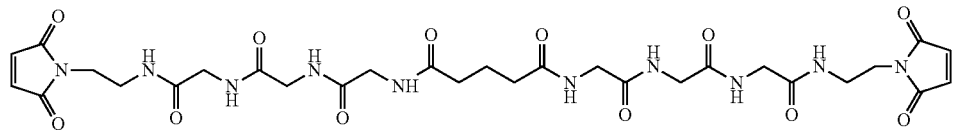

(VI-l)

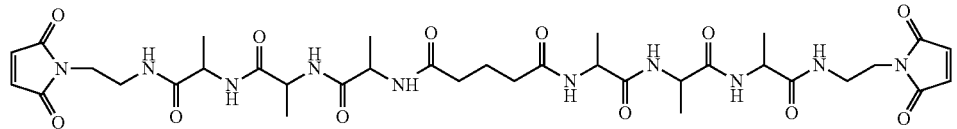

(VI-m)

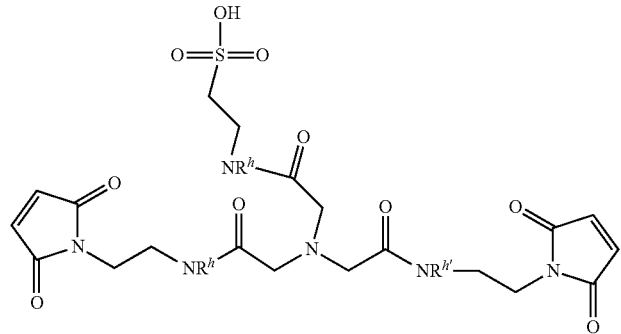

(VI-n)

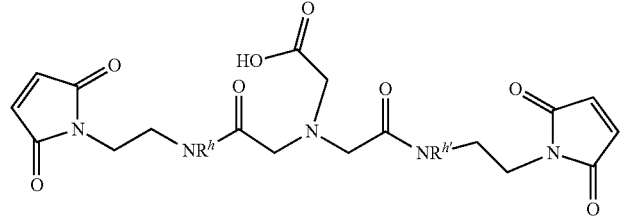

(VI-o)

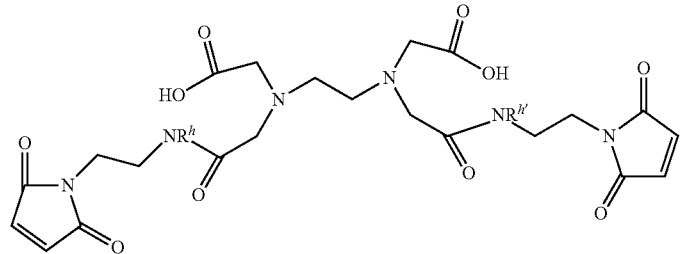

(VI-p)

, and

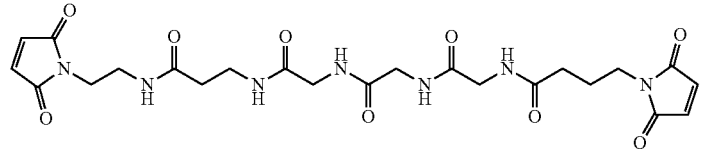

(VI-q)

or a salt (e.g., a pharmaceutically acceptable salt) thereof, in which the variables are as defined in the fifth embodiment.

In a twenty-third specific embodiment, Formula (VI'), (VI), (VI-a'), (VI-a), (VI-b'), (VI-b), (VI-c'), (VI-c), (VI-d'), (VI-d), (VI-e'), (VI-e), (VI-f'), (VI-f), (VI-g'), (VI-g), (VI-h'), (VI-h), (VI-i'), (VI-i), (VI-j'), (VI-j), (VI-k'), (VI-k), (VI-n), (VI-o), or (VI-p), $R^h$ and $R^{h'}$, for each occurrence, are independently H or methyl; and the remainder of the variables are as defined in the fifth embodiment or each of its alternative embodiments or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second specific embodiment.

In a twenty-fourth specific embodiment, Formula (VI'), (VI), (VI-a'), (VI-a), (VI-b'), (VI-b), (VI-c'), (VI-c), (VI-d'), (VI-d), (VI-e'), (VI-e), (VI-f'), (VI-f), (VI-g'), (VI-g), (VI-h'), (VI-h), (VI-i'), (VI-i), (VI-j'), (VI-j), (VI-k'), (VI-k), (VI-n), (VI-o), or (VI-p), $R^h$ and $R^{h'}$ are each H; and the remainder of the variables are as defined in the fifth embodiment or each of its alternative embodiments or its first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third specific embodiment.

In a twenty-fifth specific embodiment, in Formula (VI'), (VI), (VI-a'), (VI-a), (VI-b'), (VI-b), (VI-c'), (VI-c), (VI-d'), (VI-d), (VI-e') or (VI-e), m and n, for each occurrence, are independently an integer between 2 and 5; and the remainder of the variables are as defined in the fifth embodiment or each of its alternative embodiments or its first, second, third, fourth, fifth, sixth, seventh, eighth, ninth, tenth, eleventh, twelfth, thirteenth, fourteenth, sixteenth, eighteenth, nineteenth, twentieth, twenty-first, twenty-third, or twenty-fourth specific embodiment. Preferably, m and n are both 2.

Production of Cell-Binding Agent-Drug Conjugates

The conjugates of the present invention can be prepared according to any known method in the art. See, for example, WO 2009/134977, U.S. Pat. Nos. 7,811,572, 6,441,163, 7,368,565, 8,163,888, U.S Publication Nos. 2006/0182750, 2011/0003969, 2012/0253021 and Widdison, W. C. et al., "Semisynthetic maytansine analogues for the targeted treatment of cancer," *J. Med. Chem.* (2006) 49(14):4392-4408. In one embodiment, the conjugates of the present invention can be prepared by reacting a cell-binding agent with a drug-linker compound (e.g., cytotoxic compounds of Formula (IV'), (IV), (V'), (V), (X') or (X)) having a reactive moiety capable of forming a covalent bond with the cell-binding agent to form a cell-binding agent-cytotoxic agent conjugate. The conjugate can then be purified. The drug-linker compound can be generated in situ and used to react with the antibody without purification. Alternatively, the drug-linker compound can be generated and purified before conjugating to the cell-binding agent.

In another embodiment, the conjugates of the present invention can be prepared by: a) reacting a cell-binding agent with a linker compound (e.g., that of formula (VI'), (VI), (VII'), (VII), (XI') or (XI)) to form a modified cell-binding agent having the linkers covalently bound thereto; b) optionally purifying the modified cell-binding agent; c) conjugating a cytotoxic agent to the modified cell-binding agent to form the cell-binding agent-cytotoxic compound conjugate of the present invention; and d) purifying the cell-binding agent-cytotoxic compound conjugate.

In another embodiment, the conjugate of the present invention can be prepared by mixing together a cell-binding agent, a cytotoxic agent and a linker compound. Preferably, the cell-binding agent is contacted with a cytotoxic agent first to form a mixture comprising the cell-binding agent and the cytotoxic agent, followed by contacting the mixture with a linker compound (e.g., compounds of Formula (VI'), (VI), (VII'), (VII), (IX') or (IX)) to form the cell-binding agent-cytotoxic compound conjugate. The conjugate can then be purified.

Any purification methods known in the art can be used to purify the conjugates of the present invention (see, for example, *Bioconjugate Techniques,* 2nd Edition by Greg T. Hermanson, published by Academic Press, Inc., 2008). In one embodiment, the conjugates of the present invention can be purified using tangential flow filtration (TFF), non-adsorptive chromatography, adsorptive chromatography, adsorptive filtration, selective precipitation, high performance liquid chromatography (HPLC), dialysis or any other suitable purification process, as well as combinations thereof.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), His-Tag metal affinity resins, anti-FLAG affinity resins, and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. For example, size-exclusion chromatography can be used for purifying the conjugates of the invention. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment, when the cell-binding agent is an epitope-tagged Avibody, the conjugate can be purified using hydroxyl apatite chromatography, size-exclusion chromatography, tangential flow filtration, gel electrophoresis, dialysis, and affinity chromatography, preferably affinity chromatography, more preferably His-tag metal affinity chromatography and anti-FLAG M2 affinity chromatography (see, for example, US 2008/0152586 and US 2012/0171115).

In another embodiment, when the cell-binding agent is a Centyrin, the conjugate can be purified using protein A purification, ammonium sulfate or ethanol precipitation, acid extraction, anion or cation exchange chromatography, phosphocellulose chromatography, hydrophobic interaction chromatography, size-exclusion chromatography, tangential flow filtration, affinity chromatography, hydroxylapatite chromatography and lectin chromatography. Alternatively, the conjugate can be purified using HPLC. Preferably, the conjugate can be purified by using affinity chromatography, more preferably His-tag metal affinity chromatography. See, for example, US 2010/0255056, US 2010/0216708 and US 2011/0274623.

In another embodiment, when the cell-binding agent is a DARPin, the conjugate can be purified by affinity chromatography, size exclusion chromatography, hydroxylapatite chromatography, tangential flow filtration, preferably affinity chromatography, more preferably His-Tag affinity chromatography. See, for example, U.S. Patent Publication Nos. 2004/0132028, 2009/0082274, 2011/0118146, and 2011/0224100, WO 02/20565 and WO 06/083275.

The number of cytotoxic compound molecule bound per cell-binding agent (e.g., antibody) molecule can be determined spectroscopically by measuring the ratio of the absorbance at 280 nm and 252 nm. An average of about 0.5-about 20 cytotoxic compounds/antibody molecule(s) can be linked by the methods described herein. In one embodiment, the average number of linked cytotoxic compound per cell-binding agent in the conjugate (i.e., average w value) is about 0.5 to about 10, about 0.5 to 2 (e.g., 0.4, 0.5, 0.6, 0.7, 0.8, 0.9, 1.0, 1.1, 1.2, 1.3, 1.4, 1.5, 1.6, 1.7, 1.8, 1.9, 2.0, or 2.1), about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 5.0 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0), about 2.5 to about 4.0, about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In Vitro Evaluation of Cytotoxicity

The cytotoxic compounds and cell-binding agent-drug conjugates of the invention can be evaluated for their ability to suppress proliferation of various cancer cell lines in vitro. The in vitro cytotoxicity assays can be conducted using methods known in the art (e.g., Widdison, W. C. et al., "Semisynthetic maytansine analogues for the targeted treatment of cancer," *J. Med. Chem.* (2006) 49(14):4392-408). For example, cells to be evaluated can be exposed to the compounds or conjugates for 1-5 days and the surviving fractions of cells measured in direct assays by known methods. $IC_{50}$ values can then be calculated from the results of the assays.

Compositions and Methods of Use

The present invention includes a composition (e.g., a pharmaceutical composition) comprising conjugates (e.g., conjugates of Formula (I'), (I), (III'), (III), (IX') or (IX)) or cytotoxic compounds (e.g., compounds of Formula (IV'), (IV), (V'), (V), (X') or (X)) described herein, and a carrier (a pharmaceutically acceptable carrier). The present invention also includes a composition (e.g., a pharmaceutical composition) comprising the conjugate of Formula (I'), (I), (III'), (III), (IX') or (IX) or the cytotoxic compound of Formula (IV'), (IV), (V'), (V), (X') or (X) and a carrier (a pharmaceutically acceptable carrier), and further comprising a second therapeutic agent. The present compositions are useful for inhibiting abnormal cell growth or treating a proliferative disorder in a mammal (e.g., human). The present compositions are also useful for treating an autoimmune disorder, a destructive bone disorder, a graft versus host disease, a transplant rejection, an immune deficiency, an inflammatory disease, an infectious disease, a viral disease, a fibrotic disease, a neurodegenerative disorder, a pancreatitis or kidney disease in a mammal (e.g., human).

The present invention includes a method of inhibiting abnormal cell growth or treating a proliferative disorder in a mammal (e.g., human) comprising administering to said mammal a therapeutically effective amount of conjugates (e.g., conjugates of formula (I'), (I), (III'), (III), (IX') or (IX)) or cytotoxic compounds (e.g., compounds of formula (IV'), (IV), (V'), (V), (X') or (X)) described herein, or a composition thereof, alone or in combination with a second therapeutic agent. In one embodiment, the proliferative disorder is cancer in general; alternatively, the proliferative disorder is cancer selected from the group consisting of breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, nonsmall-cell lung cancer, testicular cancer, Merkel cell carcinoma, glioblastoma, neuroblastoma, a cancer of a lymphatic organ, and a hematological malignancy.

Similarly, the present invention provides a method for inducing cell death in selected cell populations comprising contacting target cells or tissue containing target cells with an effective amount of the conjugates of the present invention. The target cells are cells to which the cell-binding agent of the conjugates can bind.

If desired, other active agents, such as other anti-tumor agents, may be administered along with the conjugate.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include: Comprehensive index; Manufacturer; Products (by company's or trademarked drug name); Category index; Generic/chemical index (non-trademark common drug names); Color images of medications; Product information, consistent with FDA labeling; Chemical information; Function/action; Indications & Contraindications; Trial research, side effects, warnings.

The present invention also provides methods of treating a non-cancerous condition comprising administering to a subject in need of treatment an effective amount of any of the conjugates described above. Examples of the conditions include, but not limited to, an autoimmune disorder (e.g., systemic lupus, rheumatoid arthritis, and multiple sclerosis), a graft versus host disease, a transplant rejection (e.g., a renal transplant rejection, a liver transplant rejection, a lung transplant rejection, a cardiac transplant rejection, and a bone marrow transplant rejection), an immune deficiency, an inflammatory diseases (i.e., myositis and pancreatitis), a destructive bone disorder, an infectious disease (e.g., viral infections and parasite infections), a viral disease, a fibrotic disease, a neurodegenerative disorder, or a kidney disease. In one embodiment, the condition selected from the group consisting of cancer, rheumatoid arthritis, multiple sclerosis, graft versus host disease, transplant rejection, lupus, myositis, infectious disease, and immune deficiency.

Examples of in vitro uses include treatments of autologous bone marrow prior to their transplant into the same patient in order to kill diseased or malignant cells; treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 µM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic compounds or conjugates of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 µg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

Example 1

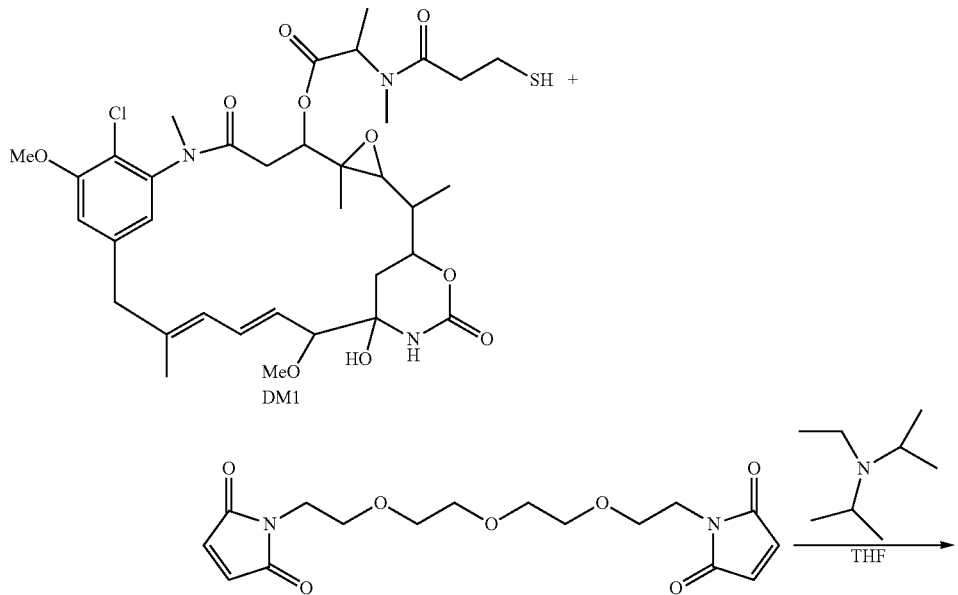

-continued

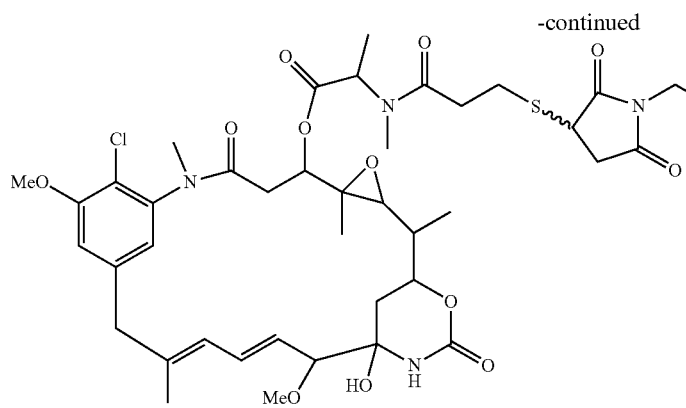

A 10 mL round bottom flask equipped with a stir bar was charged with 1,11-bis(maleimido)triethylene glycol (Thermo Scientific Cat. #22337, 50.1 mg, 0.142 mmol) and THF (1 mL). The solution stirred as DM1 (35 mg, 0.047 mmol) was added in THF (0.5 mL) followed by the addition of DIPEA (9.08 μl, 0.052 mmol). The reaction proceeded for 3 hours and was then concentrated in vacuo to give a crude oil. The desired product was isolated by semi-preparative RP-HPLC to give 14.0 mg (27.1% yield) of DM1-Mal-PEG$_3$-Mal as a colorless oil. MS: m/z found: 1112.2 (M+Na)$^+$, calculated: 1112.4; found: 1124.0 (M+Cl)$^-$, calculated: 1124.0.

Example 2

A 3 mL glass vial was charged with Bismaleimido-hexanoate (Thermo Scientific Cat. #22330, 17.9 mg, 64.8 μmol) and THF (0.75 mL). DM1 (15.9 mg, 21.6 μmol) in THF (0.75 mL) was added followed by N,N-diisopropyl-ethylamine (25.9 μmol, 4.5 μL). The vial was capped and the reaction proceeded with stirring at room temperature for 6 hours. The product was purified using a 1000 micron, 20 cm×20 cm pTLC plate eluting with 5% methanol in CH$_2$Cl$_2$, extracted and dried in vacuo to give 10 mg (45.6% yield) of the desired DM1-Mal-(CH$_2$)$_6$-Mal isolated with 90.6% purity. MS: m/z found: 1035.4 (M+Na)$^+$, calculated: 1036.4; found: 1048.3 (M+Cl)$^-$, calculated: 1048.4.

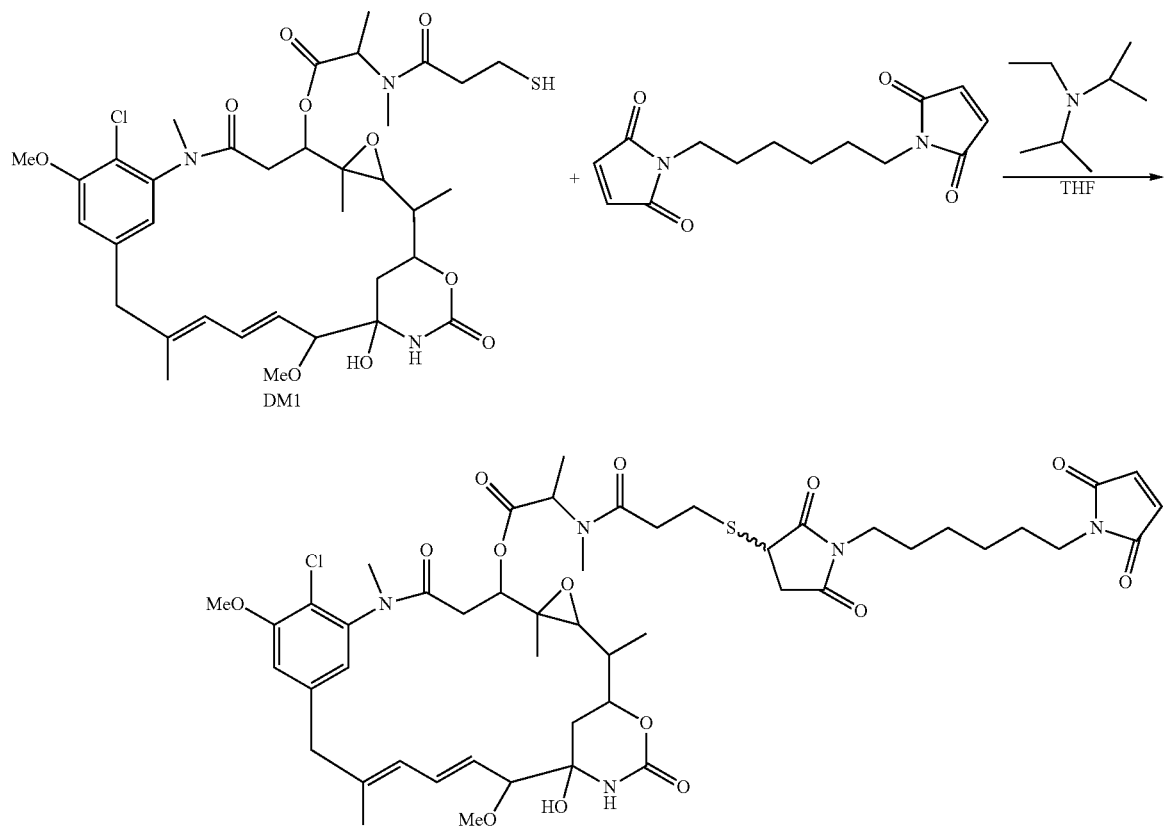

Example 3

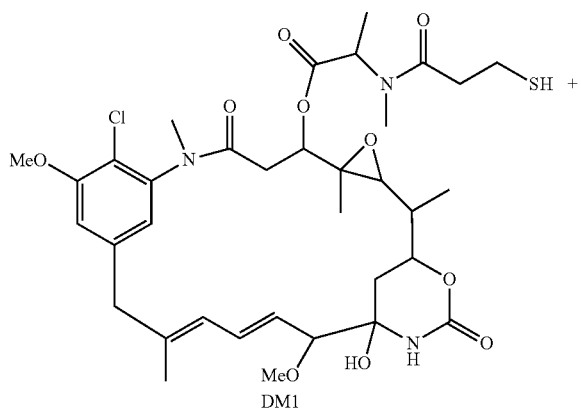

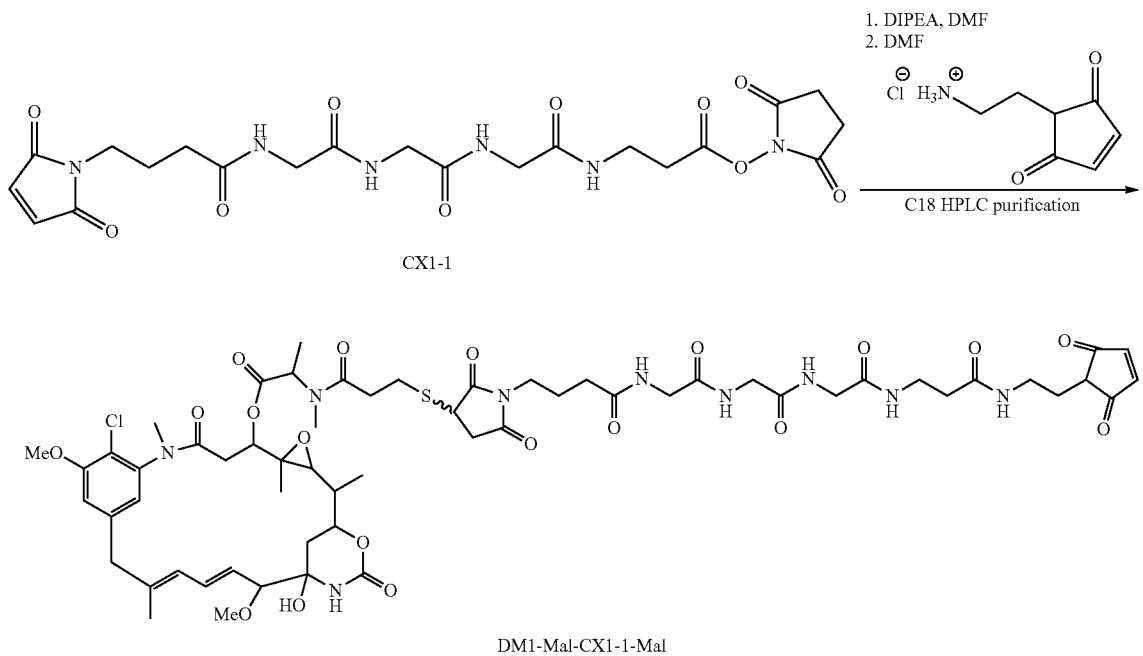

A 10 mL round bottom flask equipped with a stir bar was charged with DM1 (145.4 mg, 0.197 mmol) and DMF (1 mL). CX1-1 (prepared according to the procedure described in US2009/0274713) (103 mg, 0.197 mmol) and DIPEA (0.069 mL, 0.394 mmol) were then sequentially added. The reaction was placed under an argon atmosphere and proceeded with stirring at room temperature for 45 minutes.

2-(2,5-dioxocyclopent-3-en-1-yl)ethanaminium chloride (34.6 mg, 0.197 mmol) was then added to the reaction mixture and the reaction proceeded for an additional hour. Following reaction completion the desired product was isolated by semi-preparative C18 HPLC. Product containing fractions were combined and concentrated in vacuo to give 130.2 mg of the desired DM1-Mal-CX1-1-Mal as a white solid in 47.5% yield. Analytical C18 HPLC of the isolated product showed that the product was isolated with 92.4% purity and elutes with a retention time of 11.618 and 11.833 minutes. The isolated purity of DM1-Mal-CX1-1-Mal is 92.4%. MS: m/z found: 1307.8 (M+Na)$^+$, calculated: 1307.8; found: 1321.6 (M+Cl)$^-$, calculated: 1321.3

---

I claim:
1. A linker compound represented by the following formula, or a salt thereof:

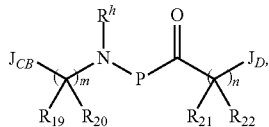

(IV-b)

wherein:
J$_{CB}$ is maleimide;
J$_D$ is maleimide;

P is selected from the group consisting of: Gly-Gly-Gly, Ala-Ala-Ala, D-Ala-Ala-Ala, Ala-D-Ala-Ala, Ala-Val-Ala, and β-Ala-Gly-Gly-Gly;

R$^h$ is H or an optionally substituted alkyl;

R$_{19}$ to R$_{22}$, for each occurrence, are independently H or an optionally substituted alkyl, and m and n are each independently 0 to 10.

2. The linker compound of claim 1, wherein R$_{19}$ to R$_{22}$ are all H.

3. The linker compound of claim 1, wherein m and n are independently an integer between 2 and 5.

4. The linker compound of claim 1, wherein the compound is represented by the following formula:

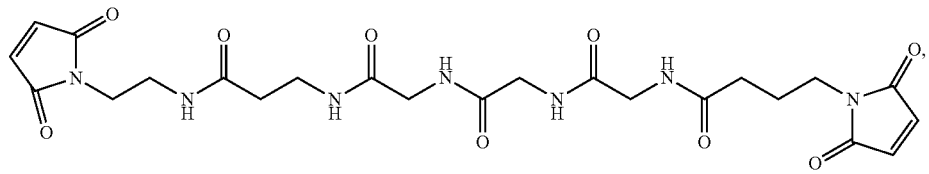 [SMILES: O=C(CCNC(=O)CNC(=O)CNC(=O)CNC(=O)CCCN1C(=O)C=CC1=O)NCCN1C(=O)C=CC1=O]

or a salt thereof.

* * * * *

UNITED STATES PATENT AND TRADEMARK OFFICE
CERTIFICATE OF CORRECTION

PATENT NO. : 9,901,647 B2
APPLICATION NO. : 14/763612
DATED : February 27, 2018
INVENTOR(S) : Wayne C. Widdison It is certified that error appears in the above-identified patent and that said Letters Patent is hereby corrected as shown below:

In the Claims

At Column 77, Claim 1, Line 6 please replace "IV-b" with "VI-b".

Signed and Sealed this
Twelfth Day of June, 2018

Andrei Iancu
*Director of the United States Patent and Trademark Office*